United States Patent
Ninomiya et al.

(10) Patent No.: US 8,678,171 B2
(45) Date of Patent: Mar. 25, 2014

(54) PASSING APPARATUS OF A WORKPIECE ASSOCIATED WITH AN ABSORBENT ARTICLE

(75) Inventors: Akihide Ninomiya, Kagawa (JP); Kazuo Ukegawa, Kagawa (JP); Hiroki Yamamoto, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 0 days.

(21) Appl. No.: 13/695,465

(22) PCT Filed: Jun. 22, 2011

(86) PCT No.: PCT/JP2011/064247
§ 371 (c)(1),
(2), (4) Date: Feb. 23, 2013

(87) PCT Pub. No.: WO2012/002214
PCT Pub. Date: Jan. 5, 2012

(65) Prior Publication Data
US 2013/0140755 A1 Jun. 6, 2013

(30) Foreign Application Priority Data
Jul. 1, 2010 (JP) .................................. 2010-151333

(51) Int. Cl.
*B65G 29/00* (2006.01)
(52) U.S. Cl.
USPC .................. 198/411; 198/397.06; 198/377.01
(58) Field of Classification Search
USPC ................................ 198/397.06, 411, 377.01
See application file for complete search history.

(56) References Cited

U.S. PATENT DOCUMENTS

| 5,988,354 | A | * | 11/1999 | Spatafora et al. | 198/471.1 |
| 6,398,006 | B1 | * | 6/2002 | Dault | 198/377.01 |
| 6,866,137 | B2 | * | 3/2005 | Ohiro et al. | 198/374 |
| 7,093,705 | B2 | * | 8/2006 | Ohiro et al. | 198/377.08 |
| 8,011,493 | B2 | * | 9/2011 | Giuliani et al. | 198/411 |
| 2008/0196564 | A1 | | 8/2008 | McCabe | |

FOREIGN PATENT DOCUMENTS

| JP | 2005298193 A | 10/2005 |
| JP | 2005298194 A | 10/2005 |
| JP | 2010063716 A | 3/2010 |

OTHER PUBLICATIONS

International Search Report for PCT/JP2011/064247, dated Oct. 4, 2011.
Extended European Search Report dated Nov. 12, 2013, corresponds to European Patent application No. 11800679.0.

\* cited by examiner

*Primary Examiner* — Kaitlin Joerger
(74) *Attorney, Agent, or Firm* — Lowe Hauptman & Ham, LLP

(57) ABSTRACT

A passing apparatus for a workpiece associated with an absorbent article receives a first sheet-like workpiece at a receiving position, changes a longitudinal direction of the first sheet-like workpiece to a direction that intersects the longitudinal direction at the time the first sheet-like workpiece is received, and discharges the first sheet-like workpiece with the changed longitudinal direction at a discharge position. The passing apparatus includes: a plurality of holding pads each having a plane section to be in contact with and for holding the first sheet-like workpiece, a revolution mechanism for causing the holding pads to revolve about a revolution axis normal to the plane section, and a spin mechanism for causing the holding pad to spin about a spin axis normal to the plane section. On an orbit of the holding pad determined by the revolution mechanism, the receiving position and the discharge position are set.

8 Claims, 10 Drawing Sheets

B-B CROSS SECTION

B-B CROSS SECTION

VIEW ALONG LINE B-B

VIEW ALONG LINE C-C

B-B CROSS SECTION

VIEW ALONG LINE B-B

VIEW ALONG LINE B-B

PASSING APPARATUS OF A WORKPIECE ASSOCIATED WITH AN ABSORBENT ARTICLE

RELATED APPLICATIONS

The present application is a National Phase of International Application Number PCT/JP2011/064247, filed Jun. 22, 2011, and claims priority from Japanese Application Number 2010-151333, filed Jul. 1, 2010.

TECHNICAL FIELD

The invention relates to a passing apparatus of a workpiece associated with an absorbent article such as a disposable diaper.

BACKGROUND ART

In a conventional manufacturing line of an absorbent article such as a disposable diaper, the operation is performed in which a first sheet-like workpiece 10 associated with an absorbent article is received from the previous process, the longitudinal direction thereof is changed by 90° from the original state, and the first sheet-like workpiece 10 is discharged to the following process, etc. This operation is performed by a 90-degree turning drum apparatus 230 as shown in a side view of FIG. 10A.

The main body of the 90-degree turning drum apparatus 230 is a rotating drum 231 which is driven and rotates about a horizontal axis C231 along the width direction of the manufacturing line (a direction perpendicular to the transporting direction; hereinafter referred to as the CD direction). On the outer periphery of the rotating drum 231, holding pads 233, 233,... which suck and hold the first sheet-like workpieces 10 are disposed at a plurality of positions in the rotating direction Dc. Each holding pad 233 is configured to spin about its own spin axis C233 along the rotation-radius direction Dr of the rotating drum 231. Further, each holding pad 233 has a holding surface 233a which sucks and holds the first sheet-like workpiece 10, the holding surface 233a facing radially outward in the rotation-radius direction Dr.

At a predetermined position Qin of the rotating drum 231 in the rotating direction Dc, the receiving position Qin is set at which the first sheet-like workpiece 10 is received from the previous process. At a predetermined position Qout on the downstream side of the position Qin, the discharge position Qout is set at which the received first sheet-like workpiece 10 is discharged to the following process. For example, at the receiving position Qin, a transporting roll 250 that is driven and rotates is arranged facing the outer circumferential surface of the rotating drum 231; the transporting roll 250 transports a single sheet of the first sheet-like workpiece 10 to the receiving position Qin with the longitudinal direction of the first sheet-like workpiece 10 pointing in the transporting direction. On the other hand, at the discharge position Qout, a suction roll 260 that is driven and rotates is arranged facing the outer circumferential surface of the rotating drum 231; the suction roll 260 can receive the first sheet-like workpiece 10 by suction from the outer circumferential surface 260a of the suction roll 260.

The 90-degree turning drum apparatus 230 having the abovementioned configuration works as follows: when the holding pad 233 passes the receiving position Qin, a single sheet of the first sheet-like workpiece 10 is received from the transporting roll 250 at the position Qin by sucking onto the holding surface 233a; thereafter, while the holding pad 233 is moving to the discharge position Qout, the longitudinal direction of the first sheet-like workpiece 10 changes to the CD direction by the 90-degree rotation of the holding pad 233 about the spin axis C233; when the holding pad 233 passes the discharge position Qout, the first sheet-like workpiece 10 whose longitudinal direction points in the CD direction is discharged to the suction roll 260 (see [PTL 1]).

CITATION LIST

Patent Literature

[PTL 1] Japanese Patent Application Laid-open Publication No. 2005-298193

SUMMARY OF THE INVENTION

Technical Problem

Generally, the holding surface 233a of the holding pad 233 is substantially arcuate so that, at the receiving position Qin, the holding surface 233a fits a circular trace Tr233 of the movement of the holding pad 233 in the rotating direction Dc. Therefore, at the receiving position Qin, a clearance between the portions of the holding surface 233a receiving the first sheet-like workpiece 10 and the outer circumferential surface 250a of the transporting roll 250 is maintained to be substantially equally spaced through the entire length of the substantially arcuate surface of the holding surface 233a in the arcuate direction. This prevents the first sheet-like workpiece 10 from creasing when receiving the workpiece 10.

However, as shown in FIG. 10B (a view along arrows B-B in FIG. 10A), at the discharge position Qout, a clearance between the first sheet-like workpiece 10 held by the holding pad 233 and the outer circumferential surface 260a of the suction roll 260 differs in different positions in the CD direction because the arcuate direction of the holding surface 233a points in the CD direction. For example, at the center 233ac in the CD direction, the clearance is small; at both ends 233ae and 233ae in the CD direction, the clearance is large. Therefore, the foregoing difference of the clearances may cause the first sheet-like workpiece 10 to crease when the workpiece 10 is discharged at the discharge position Qout.

The abovementioned clearance difference in different positions in the CD direction can be avoided by changing the shape of the holding surface 233a of the holding pad 233 to a flat surface 234a (see a section 234a indicated by a double-dotted chain line in FIG. 10A) from the foregoing substantially arcuate surface. However, in this case, when the holding pad 233 is passing the receiving position Qin, a clearance between the holding surface 234a and the transporting roll 250 changes as the holding pad 233 moves in the rotating direction Dc. For example, when the central section 234ac of the holding pad 233 in the rotating direction Dc passes the receiving position Qin, the clearance is large; when the downstream section 234ae or the upstream section 234ae passes the receiving position Qin, the clearance is small. This may cause the first sheet-like workpiece 10 to crease when workpiece 10 is received.

That is, with the foregoing configuration of the 90-degree turning drum apparatus 231, at either of the receiving position Qin and the discharge position Qout, the first sheet-like workpiece 10 can be prevented from creasing, but it is difficult to do so at both positions Qin and Qout.

The invention has been made in view of the above conventional problems, and an advantage thereof is to provide a passing apparatus which can effectively prevent the first sheet-like workpiece from creasing when receiving and discharging the first sheet-like workpiece.

Solution to Problem

An aspect of the invention to achieve the above advantage is a passing apparatus of a workpiece associated with an absorbent article that receives at a receiving position a first sheet-like workpiece being transported in a transporting direction, changes a longitudinal direction of the first sheet-like workpiece to a direction that intersects the longitudinal direction of the timing when the first sheet-like workpiece is received at the receiving position, and discharges at a discharge position the first sheet-like workpiece whose longitudinal direction is changed, including:

a plurality of holding pads having a plane section that is in contact with a surface of the first sheet-like workpiece and holds the first sheet-like workpiece;

a revolution mechanism that causes the holding pad to revolve about a revolution axis parallel to a normal direction of the plane section; and a spin mechanism that causes the holding pad to spin about a spin axis parallel to the normal direction of the plane section, wherein on an orbit of the holding pad determined by the revolution mechanism, the receiving position and the discharge position are set, at the receiving position, the longitudinal direction of the first sheet-like workpiece points in the transporting direction, the holding pad includes a holding surface in which the plane section is included, the holding surface is formed so that a longitudinal direction and a width direction thereof are respectively aligned with a longitudinal direction and a width direction of the holding pad, the holding pad passes the receiving position on the orbit by a movement of the holding pad along the transporting direction in a state where the spin mechanism causes the longitudinal direction of the holding pad to point in a direction parallel to the transporting direction of the first sheet-like workpiece, the holding pad passes the discharge position on the orbit by a movement of the holding pad in the direction parallel to the transporting direction in a state where the spin mechanism causes the longitudinal direction of the holding pad to point in a direction perpendicular to the longitudinal direction of the holding pad at the receiving position, when a downstream end of the holding pad in a revolving direction passes the receiving position, the holding pad associated with the downstream end is in a straight line with an adjacent holding pad positioned on a downstream side of the holding pad in the revolving direction and a space between the downstream end and an upstream end of the adjacent holding pad becomes smallest within an entire edge of the orbit, and after the downstream end passes the receiving position, the space is enlarged.

Other features of this invention will become apparent from the description in this specification and the attached drawings.

Effects of the Invention

According to the invention, the first sheet-like workpiece can be effectively prevented from creasing when receiving and discharging the first sheet-like workpiece.

MODE FOR CARRYING OUT THE INVENTION

Figure 1A:
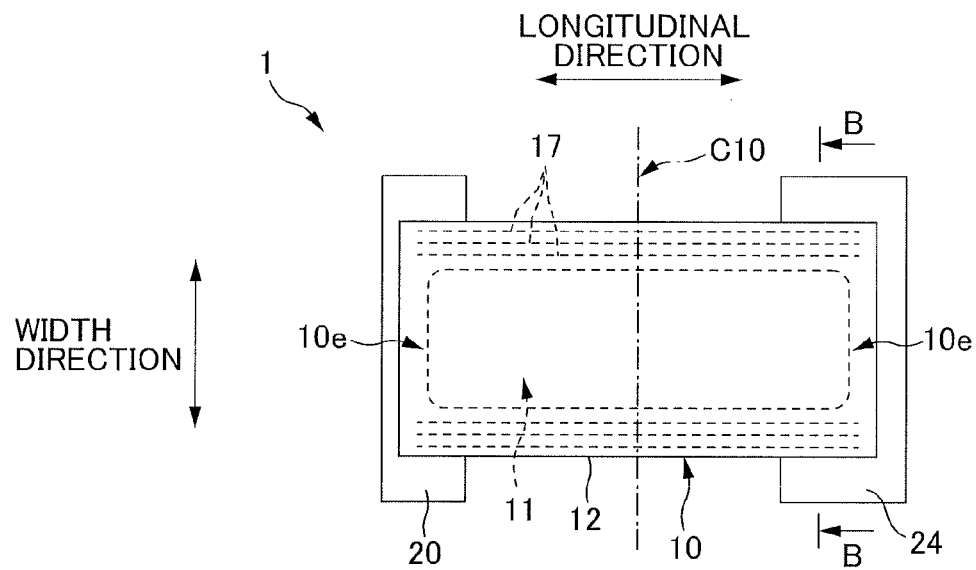
FIG. 1A is a plan view of a disposable diaper 1 in its opened condition.

At least the following matters will be made clear by the description in the present specification and the accompanying drawings.

A passing apparatus of a workpiece associated with an absorbent article that receives at a receiving position a first sheet-like workpiece being transported in a transporting direction, changes a longitudinal direction of the first sheet-like workpiece to a direction that intersects the longitudinal direction of the timing when the first sheet-like workpiece is received at the receiving position, and discharges at a discharge position the first sheet-like workpiece whose longitudinal direction is changed, including:

a plurality of holding pads having a plane section that is in contact with a surface of the first sheet-like workpiece and holds the first sheet-like workpiece;

a revolution mechanism that causes the holding pad to revolve about a revolution axis parallel to a normal direction of the plane section; and a spin mechanism that causes the holding pad to spin about a spin axis parallel to the normal direction of the plane section, wherein on an orbit of the holding pad determined by the revolution mechanism, the receiving position and the discharge position are set, at the receiving position, the longitudinal direction of the first sheet-like workpiece points in the transporting direction, the holding pad includes a holding surface in which the plane section is included, the holding surface is formed so that a longitudinal direction and a width direction thereof are respectively aligned with a longitudinal direction and a width direction of the holding pad, the holding pad passes the receiving position on the orbit by a movement of the holding pad along the transporting direction in a state where the spin mechanism causes the longitudinal direction of the holding pad to point in a direction parallel to the transporting direction of the first sheet-like workpiece, the holding pad passes the discharge position on the orbit by a movement of the holding pad in the direction parallel to the transporting direction in a state where the spin mechanism causes the longitudinal direction of the holding pad to point in a direction perpendicular to the longitudinal direction of the holding pad at the receiving position, when a downstream end of the holding pad in a revolving direction passes the receiving position, the holding pad associated with the downstream end is in a straight line with an adjacent holding pad positioned on a downstream side of the holding pad in the revolving direction and a space between the downstream end and an upstream end of the adjacent holding pad becomes smallest within an entire edge of the orbit, and after the downstream end passes the receiving position, the space is enlarged.

With such a passing apparatus of a workpiece associated with an absorbent article, the orbit of the holding pad is on a plane parallel to the plane section. That is, at the receiving position and the discharge position, the plane section of the holding pad moves in parallel on a plane parallel to the foregoing plane section. Further, when the holding pad is spinning to change the longitudinal direction of the first sheet-like workpiece, the plane section is maintained on the same plane mentioned above.

Thus, at the receiving position, a clearance between the plane section of the holding pad and a device for passing the first sheet-like workpiece to the holding pad (e.g., a cutter roll device) can be more easily maintained to be equally spaced through the entire length thereof in a passing direction in which the holding pad is passing at the receiving position and in a direction perpendicular to the abovementioned passing direction. This can effectively prevent the workpiece from creasing when the plane section receives the first sheet-like workpiece. Further, in the same way, at the discharge position, a clearance between the plane section and a device for discharging the first sheet-like workpiece (e.g., a pressing roll device) can be more easily maintained to be equally spaced through the entire length thereof in a passing direction in which the holding pad is passing at the discharge position and in a direction perpendicular to the above-mentioned passing direction. This can effectively prevent the workpiece from creasing when the holding pad discharges the first sheet-like workpiece from the plane section.

Therefore, the passing apparatus having the foregoing configuration makes it possible to effectively prevent the first sheet-like workpiece from creasing when passing the first sheet-like workpiece.

Further, throughout the period of receiving the first sheet-like workpiece which is being transported along the longitudinal direction, the longitudinal direction of the holding pad is maintained in the longitudinal direction of the first sheet-like workpiece. Also, the holding pad is moving in a state where the moving direction is maintained along the transporting direction of the first sheet-like workpiece. Therefore, the holding pad can smoothly receive the first sheet-like workpiece using the total longitudinal length of the pad.

Furthermore, throughout the period of discharging the first sheet-like workpiece, the longitudinal direction of the holding pad is maintained in a direction perpendicular to the longitudinal direction of the holding pad at the receiving position. Also, the holding pad is moving in a state where the moving direction is maintained parallel to the transporting direction. Therefore, the holding pad can smoothly discharge the first sheet-like workpiece in a state where the longitudinal direction of the first sheet-like workpiece is in a direction perpendicular to the transporting direction at the receiving position.

Further, when the first sheet-like workpieces are continuously supplied in a state where there is no or a narrow space between the adjacent first sheet-like workpieces, the holding pad can receive immediately each first sheet-like workpiece while the state being maintained. Furthermore, when a first sheet-like workpiece is discharged, the first sheet-like workpiece can be discharged while having a certain space between itself and the first sheet-like workpiece which is discharged immediately before.

In such a passing apparatus of a workpiece associated with absorbent article, desirably, the revolution mechanism includes
  a rotating member that is driven and rotates about a first axis parallel to the revolution axis, and
  a drive mechanism that changes a rotation radius of the holding pad from the first axis based on a rotating motion of the rotating member, the holding pad rotating about the first axis together with the rotating member.

With such a passing apparatus of a workpiece associated with an absorbent article, the holding pad can revolve about the revolution axis based on the rotating motion of the rotating member.

In such a passing apparatus of a workpiece associated with absorbent article, desirably, the orbit has a straight-line path along the transporting direction, the receiving position is set in the straight-line path, and an upstream section and a downstream section of the straight-line path at the receiving position each have a length equal to or more than half of a longitudinal length of the holding pad.

With such a passing apparatus of a workpiece associated with an absorbent article, the holding pad is moving, based on the foregoing straight-line path, along the transporting direction of the first sheet-like workpiece throughout the period of passing the receiving position. Therefore, the holding pad can smoothly receive the first sheet-like workpiece.

In such a passing apparatus of a workpiece associated with absorbent article, desirably, at the receiving position, the transporting direction of the first sheet-like workpiece is parallel to a moving direction of the holding pad, at the discharge position, the holding pad discharges the first sheet-like workpiece to a second sheet-like workpiece running at the discharge position, and at the discharge position, a running direction of the second sheet-like workpiece is parallel to the moving direction of the holding pad.

With such a passing apparatus of a workpiece associated with an absorbent article, it is possible to smoothly receive the first sheet-like workpiece and to smoothly discharge the first sheet-like workpiece to second sheet-like workpiece.

In such a passing apparatus of a workpiece associated with absorbent article, desirably, the absorbent article is a diaper, the first sheet-like workpiece is an absorbent main body that is brought into contact with a crotch of a wearer and absorbs a bodily fluid when the diaper is worn, the second sheet-like workpiece is a member that covers a waist of the wearer and fixes the absorbent main body to the wearer when the diaper is worn, and the transporting direction of the first sheet-like workpiece at the receiving position is parallel to the running direction of the second sheet-like workpiece at the discharge position.

With such a passing apparatus of a workpiece associated with an absorbent article, a diaper having an absorbent main body can be manufactured.

Further, in a common manufacturing line, the transporting direction of the first sheet-like workpiece at the receiving position is parallel to the running direction of the second sheet-like workpiece at the discharge position. Therefore, a passing apparatus having the foregoing configuration can be promptly applied to the above-mentioned common manufacturing line.

In such a passing apparatus of a workpiece associated with absorbent article, desirably, the orbit has a straight-line path along the transporting direction, the receiving position is set in the straight-line path.

With such a passing apparatus of a workpiece associated with an absorbent article, the holding pad is moving, based on the foregoing straight-line path, along the transporting direction of the first sheet-like workpiece throughout the period of passing the receiving position. Therefore, the holding pad can smoothly receive the first sheet-like workpiece.

In such a passing apparatus of a workpiece associated with absorbent article, desirably, of both ends of the holding pad in the longitudinal direction, one end is defined as a first end and another end is a second end, and when the holding pad passes the receiving position, the spin mechanism adjusts an orientation of the holding pad so that the first end is always positioned downstream of the second end in the revolving direction.

With such a passing apparatus of a workpiece associated with an absorbent article, a correspondence between the front and back end sections of the first sheet-like workpiece in the transporting direction and the ends of the holding pad is fixed at the receiving position. In other words, the front end section and the back end section of the first sheet-like workpiece respectively correspond to the first end and the second end of the holding pad, and in this correspondence, the first end and the second end of the holding pad do not interchange.

Therefore, conditions such as the surface of the first end can be set to conditions optimal to receive the front end section of the first sheet-like workpiece, and conditions such as the surface of the second end can be set to conditions optimal to receive the back end section of the second sheet-like workpiece. This can prevent more effectively the first sheet-like workpiece from creasing when the holding pad receives the workpiece.

In such a passing apparatus of a workpiece associated with absorbent article, desirably, of both ends of the holding pad in the longitudinal direction, one end is defined as a third end and another end is a fourth end, and when the holding pad passes the discharge position, the spin mechanism adjusts an orientation of the holding pad so that the third end is always positioned inward from the fourth end with respect to the orbit.

With such a passing apparatus of a workpiece associated with an absorbent article, if, for example, a device for discharging the first sheet-like workpiece arranged at the discharge position (e.g., pressing roll device) has an inside portion and an outside portion with respect to the orbit, a correspondence between these portions and the ends of the holding pad is fixed. In other words, the inside portion and the outside portion associated with the device respectively correspond to the third end and the fourth end of the holding pad, and in this correspondence, the third end and the fourth end do not interchange.

Therefore, conditions such as the surface of the third end can be set to conditions optimal to discharge the first sheet-like workpiece in relation to the inside portion. Also, conditions such as the surface of the fourth end can be set to conditions optimal to discharge the first sheet-like workpiece in relation to the outside portion. This can prevent more effectively the first sheet-like workpiece from creasing when the holding pad discharges the workpiece.

Present Embodiment

The passing apparatus 30 of the present embodiment is used in a manufacturing line of disposable diapers 1, for example.

Figure 1B:
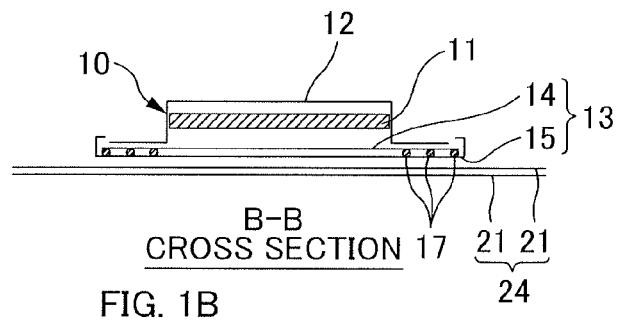
FIG. 1B is a cross-sectional view taken along line B-B in FIG. 1A.
Figure 1C:
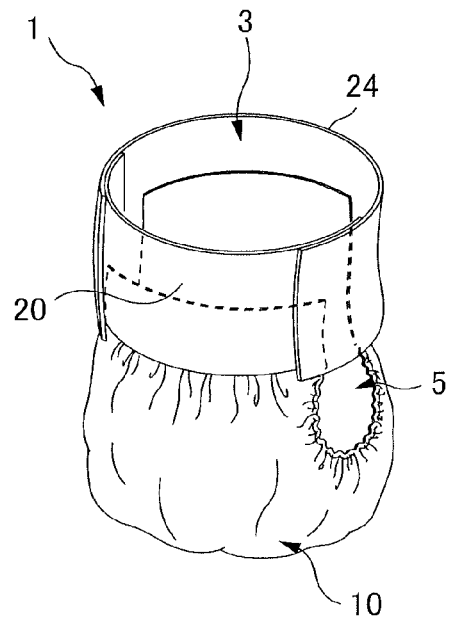
FIG. 1C is a perspective view of the diaper 1.

FIGS. 1A to 1C are explanatory diagrams of a disposable diaper 1. FIG. 1A is a plan view of a diaper 1 in its opened condition, FIG. 1B is a cross-sectional view taken along line B-B in FIG. 1A, and FIG. 1C is a perspective view of the diaper 1.

The diaper 1 includes: a stomach-side band member 20 which covers the stomach side of a wearer; a back-side band member 24 which covers the wearer's back side; and an absorbent main body 10 which is brought into contact with the wearer's crotch and absorbs bodily fluid such as urine, etc. In a diaper in its opened condition shown in FIG. 1A, the stomach-side band member 20 and the back-side band member 24 are placed parallel to each other with a certain space; both longitudinal end sections 10e and 10e of the absorbent main body 10 bridge over and are fixed to these band members. The diaper 1 in its opened condition has a substantially H-shaped appearance when seen from above.

The diaper 1 in its opened condition is two-folded at the folding position which is the longitudinal center C10 of the absorbent main body 10. Further, in this two-folded state thereof, the band members 20 and 24 opposite to each other are fastened at a portion which comes into contact with the wearer's side. Thereby, these band members 20 and 24 are connected in an annular manner; this results in the diaper 1 which has a torso opening 3 and a pair of leg openings 5 and 5 thereon and is in the worn state as shown in FIG. 1C.

As shown in FIGS. 1A and 1B, the absorbent main body 10 includes: an absorbent body 11 which is formed by shaping liquid absorbent fiber such as pulp fiber, etc into a substantially rectangular shape when viewed from the top; a surface sheet member 12 which covers the absorbent body 11 from the side closer to the skin of a wearer; and a back face sheet member 13 which covers the absorbent body 11 from the non-skin side and serves as an exterior of the diaper 1. The surface sheet member 12 is, for example, a liquid permeable, nonwoven fabric whose planer size is larger than the absorbent body 11. The back face sheet member 13 is a liquid-impermeable sheet whose planer size is larger than the absorbent body 11; as an example thereof, a sheet 13 having a two-layer structure can be provided in which a liquid-impermeable, leakage-proof sheet 14 made of polyethylene, etc and an exterior sheet 15 such as nonwoven fabric, etc are attached. In a state of sandwiching the absorbent body 11 between the back face sheet member 13 and the surface sheet member 12, the back face sheet member 13 and the surface sheet member 12 are attached to each other in a flame-like shape at the portions extending outwardly beyond four sides of the absorbent body 11. Therefore, the absorbent main body 10 are formed.

Note that, as shown in FIG. 1B, on both sides of the back face sheet member 13 in the width direction, elastic members 17 such as rubber threads are placed and fixed between the leakage-proof sheet 14 and the exterior sheet 15 while being stretched along the longitudinal direction. Thereby, around-leg gather sections having stretchability are formed on each of leg openings 5 and 5 of the diaper 1 because of the elastic members 17.

Both of the stomach-side band member 20 and the back-side band member 24 is made of a flexible sheet such as a nonwoven fabric, for example. In this example, as shown in FIG. 1B, the band members 20 and 24 are formed by placing two nonwoven fabrics 21 and 21 in tiers, and the band members 20 and 24 are attached and fixed to corresponding ends 10e and 10e of the absorbent main body 10 in the longitudinal direction. Additionally, to the band members 20 and 24, an elastic member such as a rubber thread may be fixed in a stretched manner so that the band members 20 and 24 have stretchability.

Diapers 1 of this type are finished by joining various components to a base material which is any component moving continuously in the manufacturing line. The passing apparatus 30 associated with the present embodiment is responsible for one of the processes.

Figure 2A:
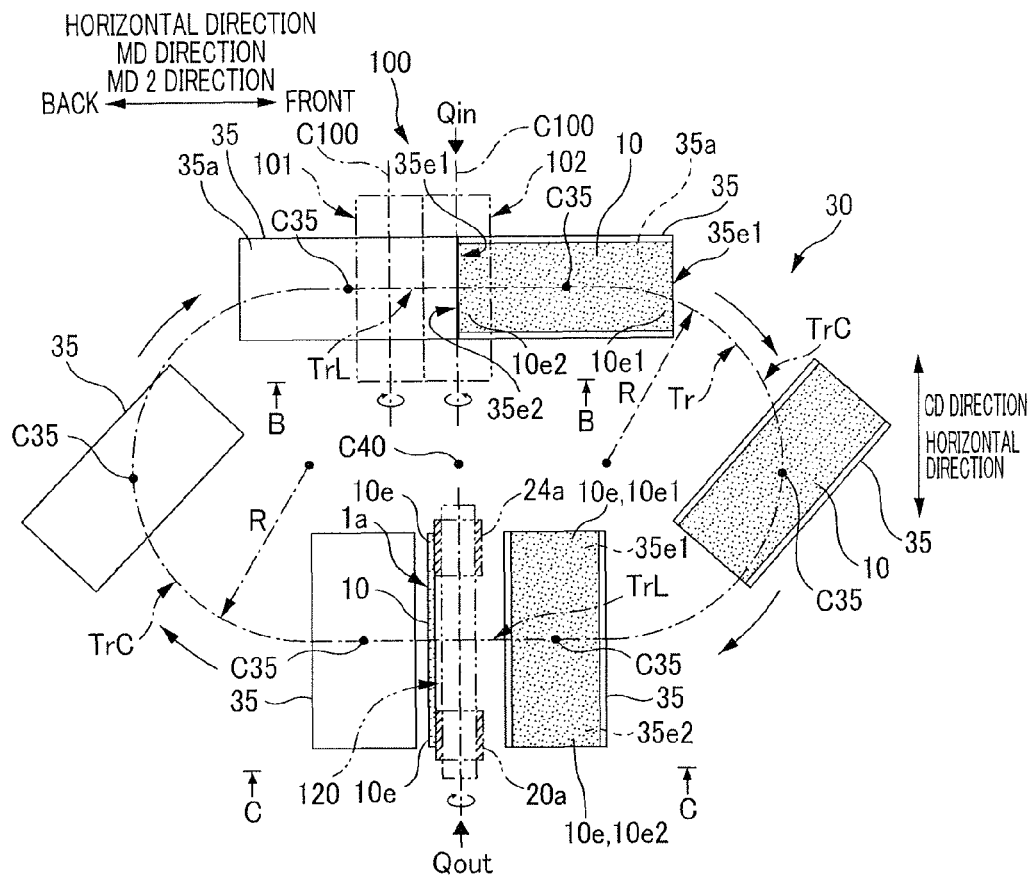
FIG. 2A is a schematically top view (plan view) of an operation in the process associated with the present embodiment.
Figure 2B:
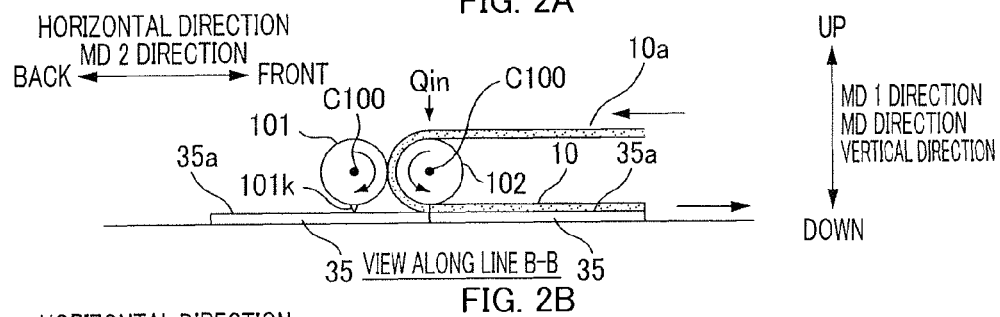
FIG. 2B is a view along arrows B-B in FIG. 2A.
Figure 2C:
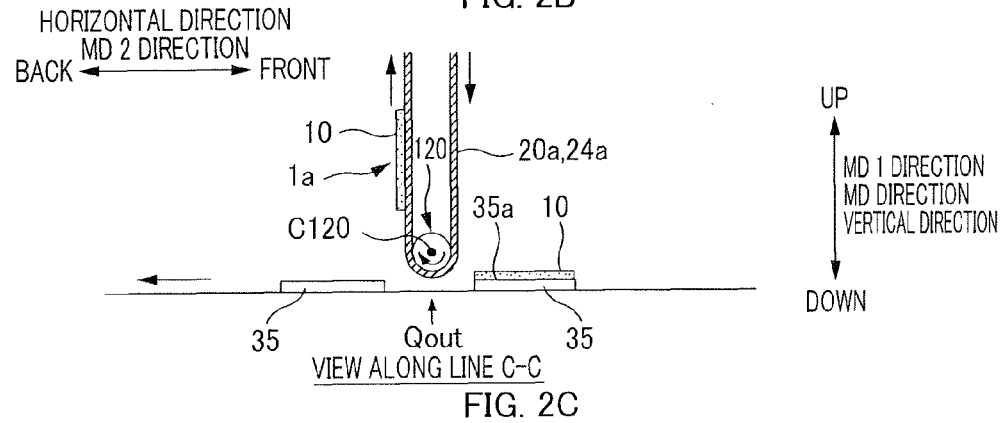
FIG. 2C is a view along arrows C-C in FIG. 2A.

FIGS. 2A to 2C are schematic diagrams of an operation in this process: FIG. 2A is a top view (plan view); FIG. 2B is a view along arrows B-B in FIG. 2A; and FIG. 2C is a view along arrows C-C in FIG. 2A.

Note that, in the following description, one direction which is horizontal is referred to as a CD direction, and any direction in a plane perpendicular to the CD direction is referred to as an MD direction, as shown in FIGS. 2A to 2C. This MD direction can be resolved into two directions: the up-down direction which is the vertical direction; and the front-and-back direction which is horizontal. For convenience, the up-down direction is referred to as an MD1 direction, and the front-and-back direction is referred to as an MD2 direction. These CD direction, MD1 direction, and MD2 direction are perpendicular to one another.

In this process, an operation by which the absorbent main body 10 bridges over and is fixed to the pair of band members 20 and 24 is performed; therefore, a semifinished product 1a of the diaper 1 has a substantially H-shaped appearance, as shown in FIG. 1A.

More specifically, as shown in FIGS. 2A and 2C, when being supplied in this process, the pair of band members 20 and 24 are continuous bodies 20a and 24a along the MD direction, which are continuously being transported in such a manner that they are lined in the CD direction with a certain space between them. Also, as shown in FIG. 2B, the absorbent main body 10 is a continuous body 10a along the MD2 direction, continuously being transported. In other words, the surface sheet member 12 and the back face sheet member 13, which is components of the absorbent main body 10, are is in a state of continuous sheets which continues in the longitudinal direction of the absorbent main body 10. At this time, between the surface sheet member 12 and the back face sheet member 13, the absorbent body 11 is placed and the absorbent bodies 11, 11, . . . are arranged at intervals in the longitudinal direction.

On the other hand, the passing apparatus 30 associated with the process includes a plurality of (6 in the figure) holding pads 35, 35, . . . which orbit in a horizontal elliptical orbit Tr in one direction (clockwise in FIG. 2A). Further, in the vicinity of a predetermined position Qin on the orbit Tr, a pair of rolls 101 and 102 are arranged as a cutter roll device 100, and the rolls continuously rotate about a rotational axis C100 pointing in the CD direction. To the nip of the pair of rolls 101 and 102, the absorbent main body 10 is supplied in a form of the continuous body 10a. The roll 102 sucks the continuous body 10a on the outer circumferential surface thereof and continuously transports it to a receiving position Qin, that is, the predetermined position Qin.

When passing the receiving position Qin in the MD2 direction, the holding pad 35 successively holds a front end portion of the continuous body 10a of the absorbent main body by sucking the portion on the upper holding surface 35a thereof. At this time, a cutting operation is performed by the cutter roll device 100 at a suitable timing and the front end portion is cut off, which results in a single sheet of the absorbent main body 10; therefore, the holding pad 35 finally receives a single sheet of the absorbent main body 10.

Thereafter, as shown in FIG. 2A, the holding pad 35 revolves in the orbit Tr without any processing operation until the holding pad 35 reaches a discharge position Qout; while moving, the holding pad 35 spins about a spin axis C35 along the up-down direction and thereby rotates horizontally. As a result, the longitudinal direction of the absorbent main body 10 change to the CD direction.

When the holding pad 35 passes the discharge position Qout, both end sections 10e and 10e of the absorbent main body 10 in the CD direction (FIG. 2A) are attached to the pair of continuous bodies 20a and 24a of the band members, which are running backward in the MD2 direction at the discharge position Qout as shown in FIG. 2C. Therefore, the absorbent main body 10 is discharged from the holding pad 35 to the pair of band members 20a and 24a, so as to form a semifinished product 1a having a substantially ladder-like shape which will later become a substantially H-shape shown in the foregoing FIG. 1A.

In this example, the absorbent main body 10 (10a) corresponds to "first sheet-like workpiece" and the continuous bodies 20a and 24a of the band members correspond to "second sheet-like workpiece."

For facilitating the understanding, FIGS. 3A to 3F show step-by-step revolving and spinning unit motions of holding pads 35. Basically, the revolution and the spin of the holding pad 35 are repeated unit motions shown in these FIGS. 3A to 3F. Note that, in these figures, the spin axis C35 of the holding pad 35 are indicated by a filled circle, and a second arm member 64 associated with a spin mechanism 60 to be described later are indicated by a solid line. Of both ends of the holding pad 35 in the longitudinal direction, the end 35e1 which is located downstream when passing the receiving position Qin is indicated by a white circle.

The configuration of the passing apparatus 30 is described in detail below.

Figure 4A:
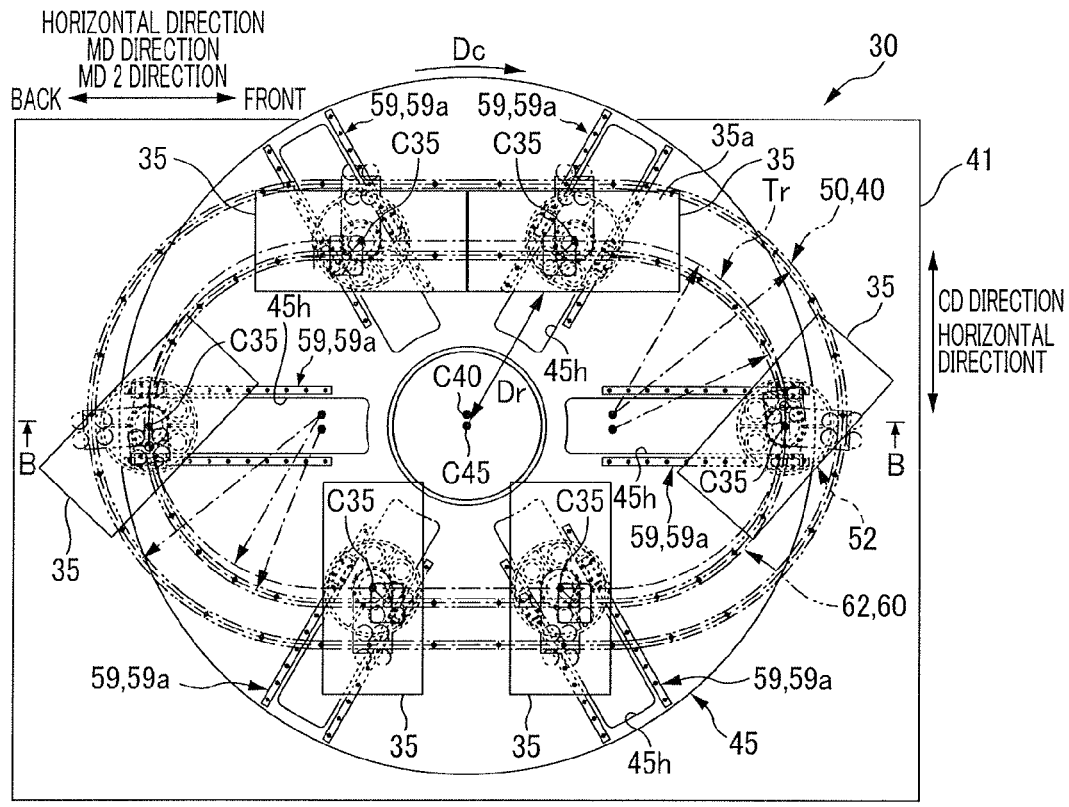
FIG. 4A is a schematic top view of the passing apparatus 30 of the present embodiment.
Figure 4B:
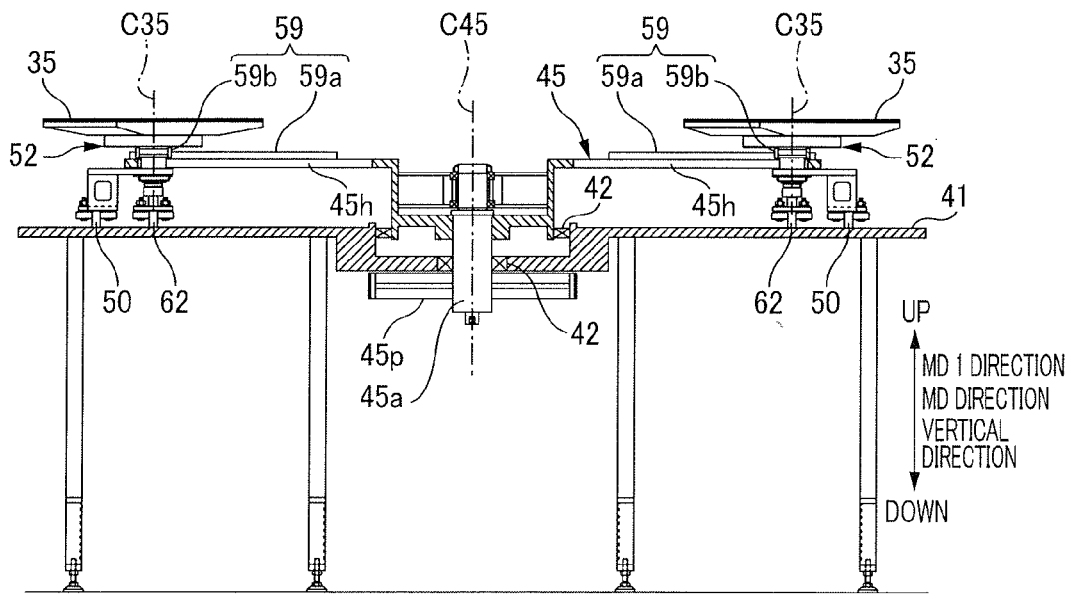
FIG. 4B is a cross-sectional view taken along line B-B in FIG. 4A.
Figure 5A:
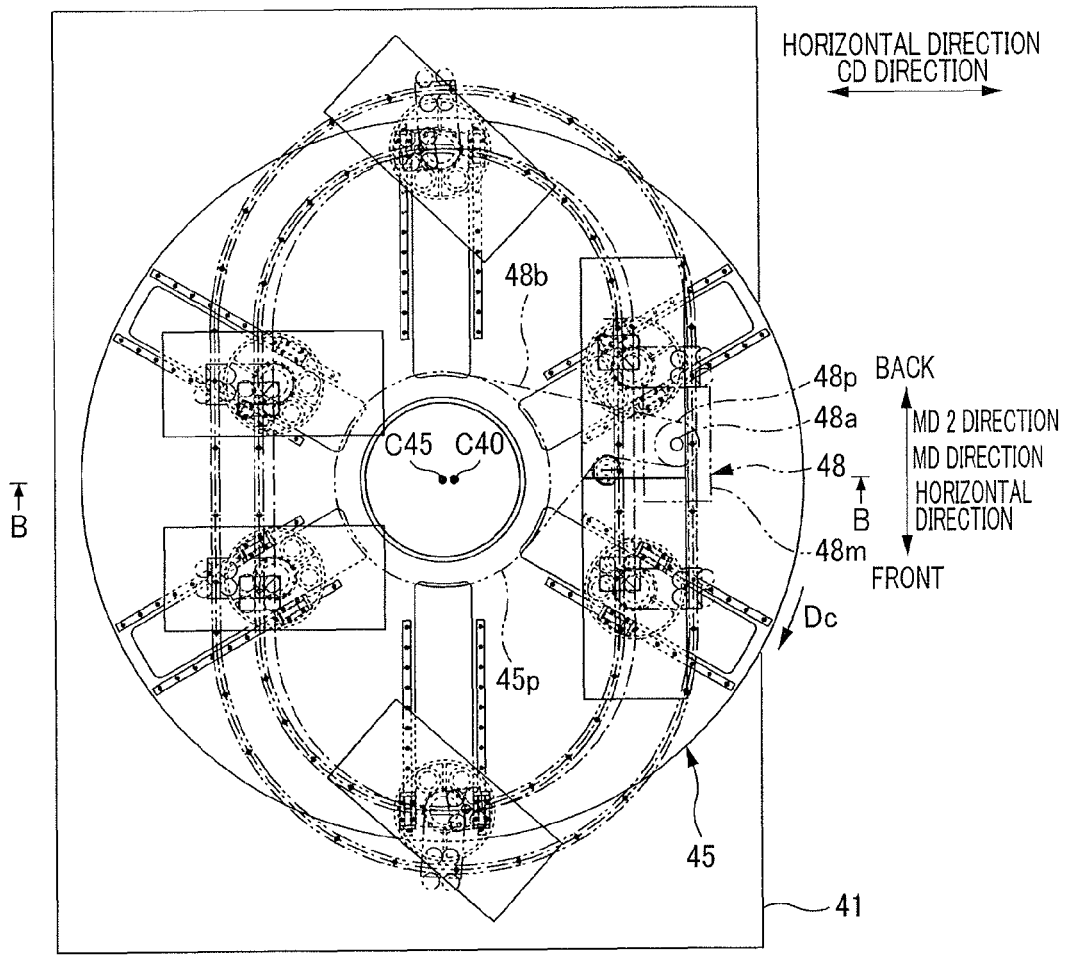
FIG. 5A is a schematic top view in which a power source 48 is added to FIG. 4A.
Figure 5B:
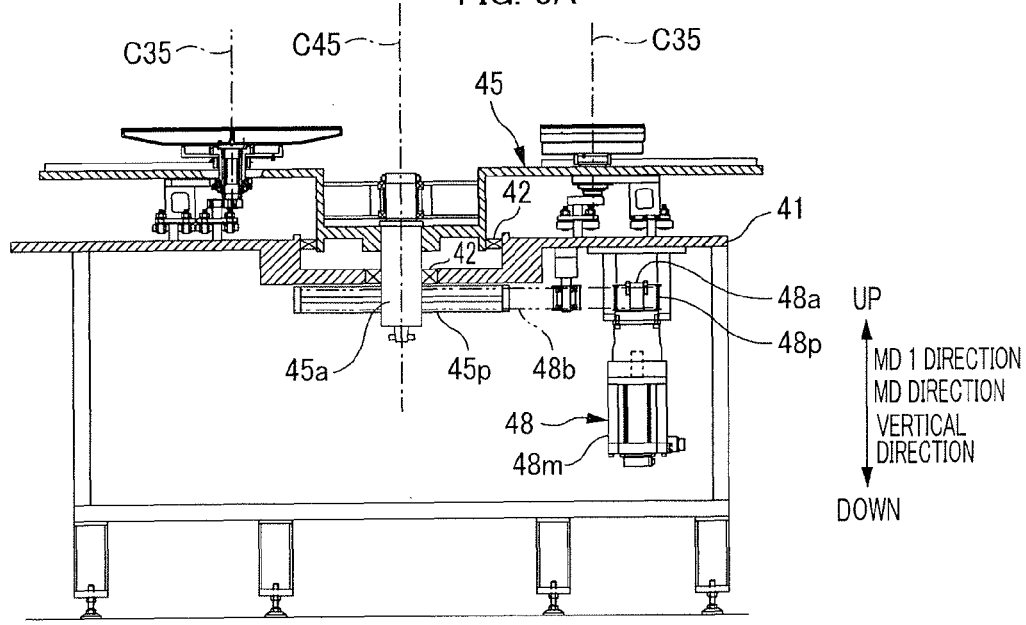
FIG. 5B is a cross-sectional view taken along line B-B in FIG. 5A.

FIGS. 4A to 5B are explanatory diagrams of the passing apparatus 30 of the present embodiment. FIG. 4A is a schematic top view of the passing apparatus 30, and FIG. 4B is a cross-sectional view taken along line B-B in FIG. 4A. FIG. 5A is another schematic top view of the passing apparatus 30; but, unlike the one in FIG. 4A, the power source 48 of the passing apparatus 30 is added in FIG. 5A. FIG. 5B is a cross-sectional view taken along line B-B in FIG. 5A. Note that, in FIGS. 4A and 5A, a part of the configuration is shown in a side view. Also, in order to avoid complications regarding the diagrams, the part of the configuration is indicated by double-dotted chain lines, and hatching of some cross-sectional parts which should be indicated by hatching is omitted.

Figure 6A:
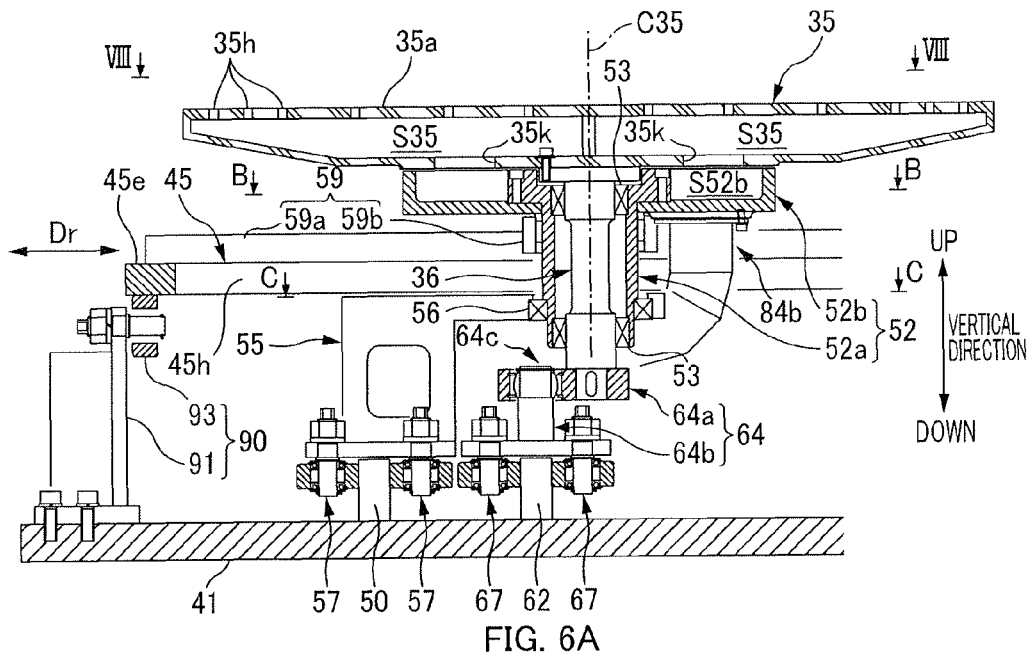
FIG. 6A is a schematic sectional view of the holding pad 35 associated with the passing apparatus 30 in the middle of the longitudinal direction thereof.
Figure 6B:
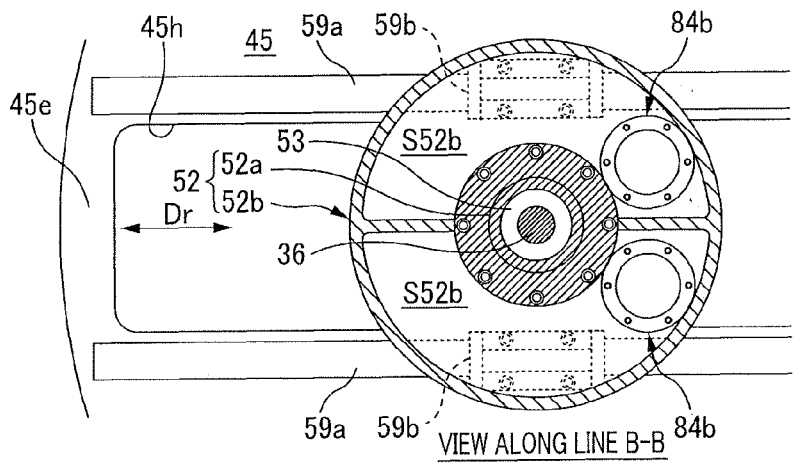
FIGS. 6B and 6C are cross-sectional views taken along line B-B and line C-C respectively in FIG. 6A.
Figure 6C:
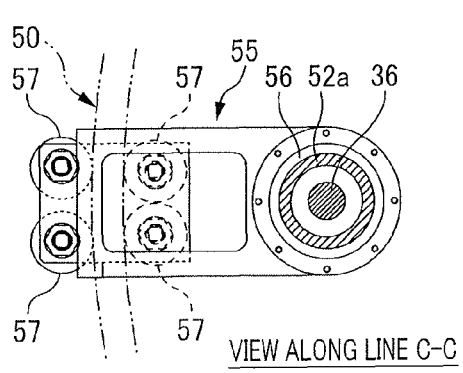

Further, FIGS. 6A to 6C are explanatory diagrams of the holding pad 35 associated with the passing apparatus 30. FIG. 6A is a schematic sectional view in the middle of the longitudinal direction of the holding pad 35, and FIGS. 6B and 6C are cross-sectional views taken along line B-B and line C-C respectively in FIG. 6A.

The passing apparatus 30 includes: a plurality of the holding pad 35, 35, . . . ; a revolution mechanism 40 which causes the plurality of holding pad 35, 35, . . . to revolve about a revolution axis C40 pointing in the up-down direction; a spin mechanism 60 which causes each holding pad 35 to spin about a spin axis C35 parallel to the revolution axis C40; and a suction mechanism 80 which provides suction to the holding surface 35a of each holding pad 35. Note that, in order to avoid complications regarding the diagrams, the suction mechanism 80 is not shown in FIGS. 4A to 5B.

<<<Revolution Mechanism 40>>>

The revolution mechanism 40 includes: a rectangular fixed table 41 which is mounted on the foundation of the manufacturing line; a circular turning table 45 (corresponding to rotating member) which is arranged above the fixed table 41 and is supported by the fixed table 41 through a bearing 42, the turning table 45 being rotatable about a first axis C45 parallel to the revolution axis C40; a power source 48 which drives and rotates the turning table 45 (see FIGS. 5A and 5B); and a first rail 50 which is fixed onto the fixed table 41 and defines the orbit Tr of the holding pad 35.

As mentioned above, the revolution axis C40 is set along the up-down direction. Therefore, the turning table 45 rotates horizontally about the first axis C45 parallel to the revolution axis C40. As shown in FIGS. 5A and 5B, the power source 48 of the foregoing rotation is a servo motor 48m, for example, which is mounted on the lower surface of the fixed table 41. The drive shaft 48a of the servo motor 48m is connected to a shaft 45a through pulleys 45p and 48p, a timing belt 48b, etc, the shaft 45a extending downwardly coaxially with the rotation center C45 of the turning table 41. Therefore, driving power is provided to the turning table 45.

As shown in FIGS. 4A and 4B, on the upper surface of the turning table 45, the plurality of holding pad 35, 35, . . . are arranged at a predetermined angular pitch along a rotating direction Dc. In the example of FIG. 4A, because the number of the holding pad 35 is 6, the holding pad 35 are arranged at the angular pitch of 60° along the rotating direction Dc. As shown in FIG. 6A, for each holding pad 35, there is its own pad supporting section 52 therebelow, and the holding pad 35 is supported by the pad supporting section 52 so as to spin. More specifically, each holding pad 35 includes a shaft 36 whose axis is the same as the spin axis C35 along the up-down direction; the shaft 36 extends downwardly from the lower surface of the holding pad 35 in an integrated manner. The shaft 36 is supported by bearings 53 and 53 in a state where the shaft 36 is inserted into a cylindrical member 52a included in the pad supporting section 52, the bearings 53 and 53 being located on the inner circumferential surface of the cylindrical member 52a. This allows the holding pad 35 to spin about the axis.

Further, as shown in FIG. 4A, each pad supporting section 52 is guided by guide members 59, such as a linear guide, so as to move linearly back and forth along the rotation-radius direction Dr on the turning table 45. That is, as shown in FIGS. 4A, 6A, and 6B, each guide member 59 includes: a pair of linear guide rails 59a and 59a which are arranged from inside to outside substantially in the rotation-radius direction Dr; and a pair of guide blocks 59b and 59b which are slidably engaged with the pair of linear guide rails 59a and 59a. Each guide block 59b is fixed to the lower surface of a no-top-bottom-closed cylinder 52b whose axis is the same as the cylindrical member 52a of the pad supporting section 52 and which is fixed in an integrated manner outside of the member 52a. Therefore, each holding pad 35 is guided through the pad supporting section 52 so as to move back and forth in the rotation-radius direction Dr of the turning table 45.

The pair of linear guide rails 59a and 59a and the pair of guide blocks 59b and 59b are arranged for each pad supporting section 52 as mentioned above. The pair of linear guide rails 59a and 59a are arranged and fixed at the angular pitch (the pitch of 60° in the example of FIG. 4A) in the rotating direction Dc of the turning table 45, as shown in FIG. 4A; the overall form has an substantially radial arrangement when viewed from above.

Further, as shown in FIG. 4A, on the upper surface of the fixed table 45, the annular first rail 50 is mounted. The first rail 50 has a function to define the orbit Tr of the holding pad 35 as mentioned above, and the rail 50 is an elliptical rail member whose planar center is the revolution axis C40. As shown in FIG. 6A, a first arm member 55 is slidably engaged with the first rail 50, and the first arm member 55 is connected to the cylindrical member 52a of the pad supporting section 52 through a bearing 56 so as to rotate relatively about the spin axis C35.

Therefore, when the turning table 45 rotates in a direction (clockwise, for example) as shown in FIG. 4A, the holding pads 35 also turn together with the turning table 45 in the direction mentioned above because the holding pads 35 are restricted by the foregoing guide members 59 so as not to move relatively in the rotating direction Dc of the turning table 45. During this time, each holding pad 35 is engaged with the first rail 50 through the pad supporting section 52 and the first arm member 55. Therefore, the first rail 50 gives to the holding pad 35 the force necessary to move inward and outward in the rotation-radius direction Dr. Thereby, into the holding pad 35, a traveling motion in the rotation-radius direction Dr is entered as well as the foregoing rotating motion in the rotating direction Dc. As a result, the holding pad 35 orbits in the elliptical orbit Tr. The orbit Tr will be described later.

In the present embodiment, as shown in FIGS. 6A and 6C, the first arm member 55 includes a plurality of cam followers 57, 57, . . . which roll while being in contact with the side surfaces of the first rail 50; through these cam followers 57, 57, . . . , the first arm member 55 is engaged with the first rail 50. That is, in order to grip the first rail 50 between a pair of the cam followers 57 and 57 from both sides, the cam followers 57, 57, . . . are disposed on both sides of the first rail 50 in pairs, for example, two each on both sides. Therefore, the first arm member 55 and the first rail 50 are smoothly engaged with each other having low frictional resistance.

Further, as shown in FIGS. 4A, 4B, 6A, and 6B but not mentioned above, the turning table 45 has a substantially rectangular opening 45h along and between the pair of linear guide rails 59a and 59a, the opening 45h being formed completely through the turning table 45 in the up-down direction. Through the opening 45h, the cylindrical member 52a of the pad supporting section 52 is arranged on the turning table 45, and the lower part of the cylindrical member 52a is positioned in the vicinity of the first rail 50 of the fixed table 45. Therefore, as mentioned above, the first arm member 55 can connect the cylindrical member 52a and the first rail 50 to each other.

Note that, the foregoing guide member 59, the first arm member 55, the first rail 50, and the pad supporting section 52 correspond to a drive mechanism which changes the rotation radius of the holding pad 35 from the first axis C45 based on the rotating motion of the turning table (rotating member) 45.

<<<Rotation-on-Axis Mechanism 60>>>

As shown in FIGS. 4A and 6A, the spin mechanism 60 includes: an annular second rail 62 which is mounted on the upper surface of the fixed table 41; and a second arm member 64 which are disposed for each of the holding pad 35. The second arm member 64 is engaged with the second rail 62 so as to produce the spin motion of the holding pad 35 from the rotating motion of the turning table 45, and then the arm member 64 transfers the motion to the holding pad 35.

The second rail 62 is also an elliptical rail member, and is arranged closer to the center than the first rail 50, in other words, between the first rail 50 and the revolution axis C40, for example. On the other hand, as shown in FIG. 6A, the second arm member 64 includes: a linking member 64a which is mounted to the lower end of the shaft 36 of the holding pad 35; and an engaging member 64b which is slidably engaged with the second rail. The linking member 64a and the engaging member 64b are connected to each other through a bearing member 64c which allows the pad to rotate about the vertical axis; therefore, the spin motion of the holding pad 35 is produced based on the rotating motion of the turning table 45.

In the example of FIG. 6A, in order to make the engagement between the second rail 62 and a engaging member 64b smooth, the engaging member 64b includes a plurality of cam followers 67, 67, . . . which are rolling while being in contact with the side surfaces of the second rail 62. That is, in order to grip the second rail 62 between a pair of the cam followers 67 and 67 from both sides, the cam followers 67, 67, . . . are disposed on one side and the other side of the second rail 62 respectively, for example, two each for both sides. However, the invention is not limited thereto. On each side of the rail, only one cam follower 67 may be arranged. Furthermore, the means does not necessary use the cam follower 67.

<<<Suction Mechanism 80>>>

Figure 7A:
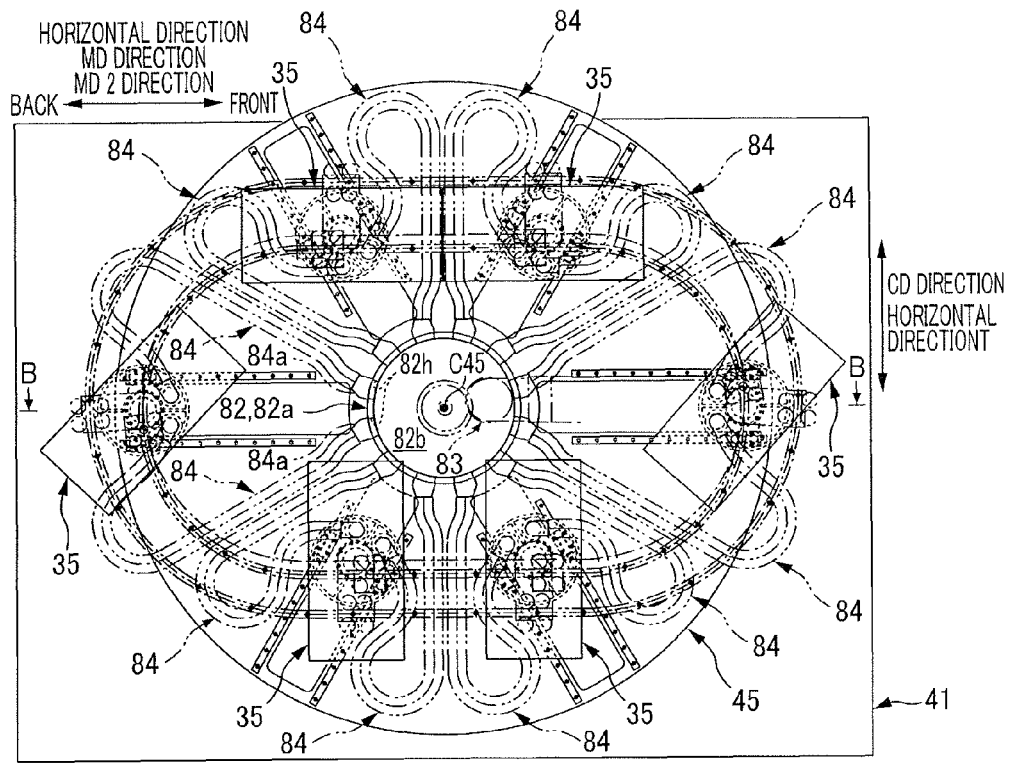
FIGS. 7A and 7B are diagrams in which the configuration of the suction mechanism 80 is added to FIGS. 4A and 4B respectively.
Figure 7B:
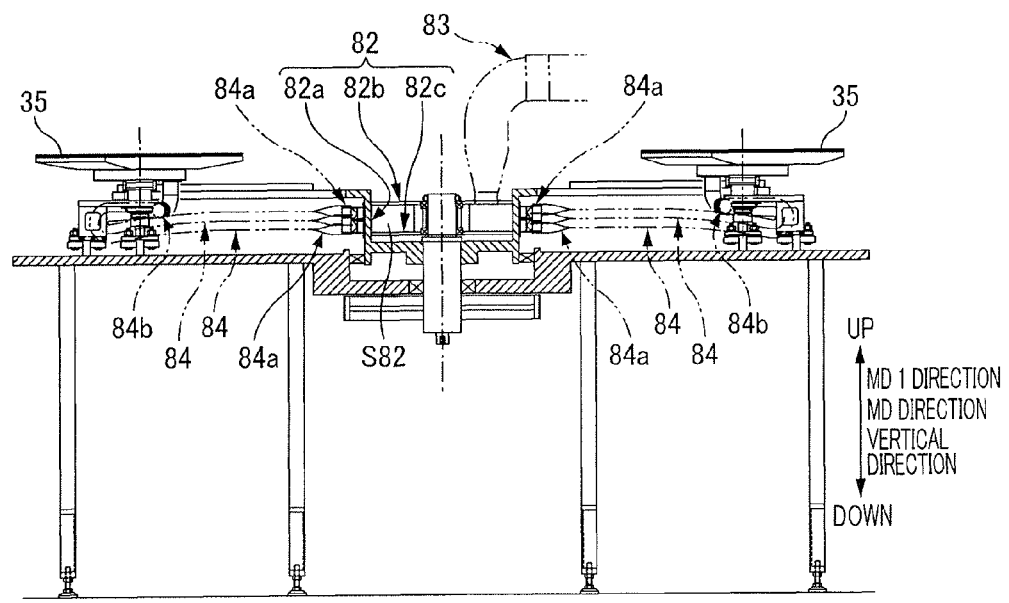
Figure 8A:
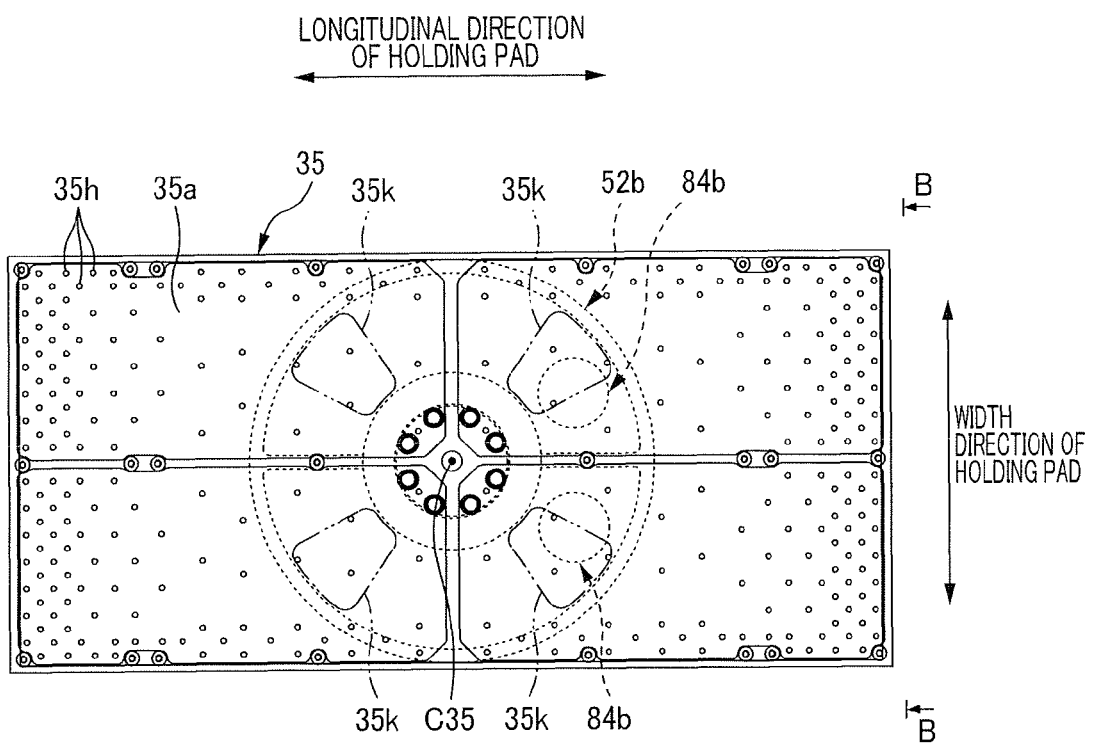
FIG. 8A a plan view along arrows VIII-VIII in FIG. 6A.
Figure 8B:
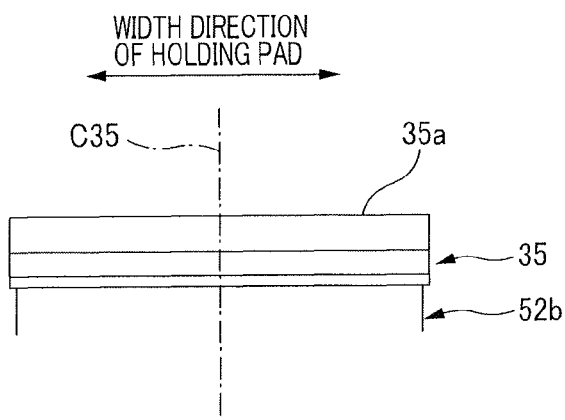
FIG. 8B is a view along arrows B-B in FIG. 8A.

FIGS. 7A and 7B are diagrams in which the configuration of the suction mechanism 80 is added to FIGS. 4A and 4B respectively. Note that, in the figures, the configuration of the suction mechanism 80 is indicated mainly by double-dotted chain lines. FIG. 8A is a plan view along arrows VIII-VIII in FIG. 6A, and FIG. 8B is a view along arrows B-B in FIG. 8A.

The suction mechanism 80 includes: a plurality of suction holes 35h, 35h, . . . formed on each of the holding pads throughout the holding surface 35a of the pad; a substantially doughnut-shaped negative-pressure chamber drum 82 disposed on the center of the turning table 45; and suction hoses 84 disposed for each of the holding pads 35. The suction hoses 84 cause the suction holes 35h of the holding pad 35 and the negative-pressure chamber drum 82 to communicate air-permeably with each other.

The main body of the negative-pressure chamber drum 82 is a cylindrical member 82a which is mounted on the turning table 45 in an integrated manner coaxially with the first axis C45, that is, the rotation center of the turning table 45. The upper and lower openings of the cylindrical member 82a are filled respectively by circular cover plates 82b and 82c; thereby, a substantially-closed space S82 is partitioned on the inner side of the cylindrical member 82a. To the upper cover plate 82b, a negative pressure source (not shown) such as a blower is connected through a suction duct 83. Therefore, the foregoing substantially-closed space S82 is maintained at negative pressure. Further, the cylindrical member 82a has through holes 82h for each suction hose 84, the through holes 82h communicating with the substantially-closed space S82. Each through hole 82h connects to the hose opening 84a of the corresponding suction hose 84 on one end of the hose 84.

On the other hand, as shown in FIG. 6A, each of the holding pads 35 has a space S35 inside thereof; the space S35 communicates with the suction holes 35h of the holding surface 35a. Further, on the lower surface of the holding pad 35, opening sections 35k are formed through which the inner space S35 communicates with an inner space S52b of the no-top-bottom-closed cylinder 52b of the pad supporting section 52 (see also FIG. 8A). The cylinder 52b connects to a hose opening 84b of the foregoing suction hose 84 on the other end of the hose 84. Therefore, the suction holes 35h connect to the substantially-closed space S82 in the negative-pressure chamber drum. As a result, the holding surface 35a has a suction force for sucking and holding an absorbent main body 1 by suction from the suction holes 35h. Note that, though two suction hoses 84 are disposed for each of the holding pads 35 in the example of FIG. 4A, the number of the hoses is not limited thereto.

<<<Holding Pad 35>>>

As shown in FIG. 8A, the outer shape of the holding pad 35 of the present embodiment is a rectangle. Also, the holding surface 35a formed on the upper surface of the holding pad 35 has a rectangular shape; the longitudinal direction and the width direction of the holding surface 35a are the same respectively as the longitudinal direction and the width direction of the holding pad 35. The holding surface 35a holds the absorbent main body 10 in surface-to-surface contact with the lower surface of the main body 10 (corresponding to the surface).

The holding surface 35a has a plane section whose normal direction is parallel to the spin axis C35; in the illustrated example, the plane section occupies the whole area of the holding surface 35a. In this example, because the spin axis C35 points in the up-down direction as mentioned above, the holding surface 35a which is the plane section is horizontal entirely. This relates to prevention of creasing the absorbent main body 10 when receiving and discharging the absorbent main body 10, which will be described later. Though, in the example of FIG. 8A, the spin axis C35 is set at the planar center of the holding surface 35a, the spin axis C35 may be located at a position slightly different from the planar center.

In the foregoing sections, the case where the suction holes 35h are formed over the substantially entire surface of the holding surface 35a is described. However, it is preferable that, concerning the distribution of the suction holes 35h, the density of the holes is high in the peripheral area of the holding surface 35a, that is, the area adjacent on all four sides, and the density in the other areas such as the central area is relatively low compared to the foregoing peripheral area, as shown in FIG. 4A. With such a distribution, the peripheral area of the absorbent main body 10 is selectively sucked by the holding surface 35a firmly. This makes it possible to prevent, without extremely increasing the negative pressure of the negative-pressure chamber drum 82, the peripheral area of the absorbent main body 10 from curling up due to the wind pressure caused by the spinning of the holding pad 35; in addition thereto, this also makes it possible to effectively prevent the absorbent main body 10 from shrinking in the longitudinal direction because of the elastic members 17 and 17 on both sides of the absorbent main body 10 in the width direction. As a result, when attaching the absorbent main body 10 to the continuous bodies 20a and 24a of the band members, the assembly accuracy can be remarkably improved.

<<<Orbit Tr and Auxiliary Devices Associated with Passing of Absorbent Main Body 10>>>

The orbit Tr described in this section is defined as one of which a representative point is the spin axis C35, which is the planar center of the holding surface 35a of the holding pad 35. In other words, the orbit Tr is the track traced by the spin axis C35. The orbit Tr is set to an elliptical shape, as indicated by a single-dotted chain line in FIG. 2A. More specifically, the orbit Tr has a pair of semicircular paths TrC and TrC on both ends in the front-and-back direction (MD2 direction) and the pair of semicircular paths TrC and TrC are connected by two parallel straight-line paths TrL and TrL along the front-and-back direction. Note that the pair of semicircular paths TrC and TrC are the same in diameter R.

On one of the two straight-line paths TrL and TrL, the receiving position Qin mentioned above is set, and one the other, the discharge position Qout is set. These receiving position Qin and discharge position Qout are set at the center of the respective straight-line paths TrL and TrL.

At the receiving position Qin, the cutter roll device 100 is located. As shown in FIG. 2B, the main body of the cutter roll device 100 is the pair of front roll 101 and back roll 102 which are arranged above the holding pad 35 in the straight-line path TrL; the rolls 101 and 102 are driven and rotate about an axis C100 along the CD direction. On the outer circumferential surface of the back roll 101, a cutter blade 101k is arranged along the CD direction which has a form like a straight blade and serves as a cutter roll 101. The front roll 102 has a circular cross section and is a flat roll whose outer circumferential surface is flat throughout the CD direction. The front roll 102 serves as an anvil roll 102 which receives the cutter blade 101k.

To the cutter roll device 100 mentioned above, the absorbent main body 10 is continuously transported in a form of the continuous body 10a from the front to the back in the MD2 direction. The continuous body 10a of the absorbent main body follows a path, for example, in which the body 10a is wrapped around the anvil roll 102 with a wrapping angle of approximately 180° from a wrapping-start position which is the top of the anvil roll 102 (12 o'clock position), then the transporting direction of the body 10a is reversed in the forward MD2 direction, and the body 10a finally separates from the outer circumferential surface of the anvil roll 102 at the bottom of the anvil roll 102 (6 o'clock position).

While being transported, the continuous body 10a of the absorbent main body is cut off by the cutter blade 101k of the cutter roll 101 at the position of the nip between the cutter roll 101 and the anvil roll 102, into a piece having substantially the same length as the total longitudinal length of the holding pad 35. Therefore, the front end portion of the continuous body 10a is cut off, which results in a single sheet of the absorbent main body 10. Even after being cut off, the portions of the absorbent main body 10 and the portions of the continuous body 10a thereof move in an integrated manner with the outer circumferential surface of the anvil roll 102 till they reach the bottom of the anvil roll 102 (6 o'clock position) because the absorbent main body 10 and the continuous body 10a thereof are sucked on the outer circumferential surface by suction of the outer circumferential surface. At the bottom of the anvil roll 102 (6 o'clock position), the portions of the absorbent main body 10 or the portions of the continuous body 10a thereof are successively discharged from the outer circumferential surface of the anvil roll 102 onto the holding surface 35a of the holding pad 35 which is moving forward along the MD2 direction. Therefore, the bottom of the anvil roll 102 (6 o'clock position) serves as the receiving position Qin, and the holding pad 35 finally receives a single sheet of the absorbent main body 10 from the cutter roll device 100.

As shown in FIG. 2A, while the holding pad 35 is passing the receiving position Qin, the moving direction of the holding pad 35 is fixed and maintained forward the front-and-back direction, which is the transporting direction of the absorbent main body 10 at the receiving position Qin. The longitudinal direction of the holding pad 35 is also fixed and maintained by means such as the spin mechanism 60 in a state where the longitudinal direction of the holding pad 35 is parallel to the MD2 direction. In other words, during an operation of receiving the absorbent main body 10, the longitudinal direction of the holding pad 35 is maintained in the same direction as the longitudinal direction of the absorbent main body 10. This allows the holding pad 35 to smoothly receive the absorbent main body 10 using the total longitudinal length of the pad. Note that, the above-mentioned fixing and maintaining of the moving direction and the longitudinal direction of the holding pad 35 while passing the receiving position Qin are based on the straight-line paths Tr50L and Tr62L, the straight-line paths which are set so that the receiving position Qin lies on the paths. This will be described later.

Further, the entire holding surface 35a of the holding pad 35 is in a horizontal plane, and the holding surface 35a moves based on the orbit Tr in the same horizontal plane as the abovementioned horizontal plane. Therefore, a clearance between the holding surface 35a and the outer circumferential surface of the anvil roll 102 is equally spaced through the entire length thereof in the CD direction (a direction perpendicular to the paper surface in FIG. 2B). And, while the portions of the holding surface 35a are passing the receiving position Qin along the MD2 direction which is a passing direction, the foregoing clearance is maintained equally through the entire length of the holding surface 35a in the MD2 direction. This can effectively prevent the absorbent main body 10 from creasing when receiving the body.

However, in some cases, the holding pad 35 may have a horizontal plane section only on a part of the holding surface 35a and not on the entire surface thereof; in other words, the holding surface 35a may have some irregularities and slopes partially on other area than the horizontal plane section. In this case, it is desirable that the peripheral area of the holding surface 35a (see, the area in which the density of the suction holes 35h is high, in the holding surface 35a of FIG. 8A) is a horizontal plane section in a flame-like shape. With this configuration, because the abovementioned clearance is maintained to be equally spaced at least on the peripheral area, the absorbent main body 10 can be sucked and held while the absorbent main body 10 is prevented from creasing. Therefore, in such a manner that the absorbent main body 10 is restricted by the peripheral area, the creasing of the absorbent main body 10 can be suppressed in the entire area of the body 10.

The configuration of the example shown in FIGS. 2A and 2B is as follows: when the downstream end 35e1 of the holding pad 35 passes the receiving position Qin, this holding pad 35 is in a straight line with an adjacent holding pad 35 positioned on the downstream side of the former holding pad 35 in the revolving direction, and at this time, a space between the downstream end 35e1 and the upstream end 35e2 of the adjacent the holding pad 35 becomes smallest within the entire edge of the orbit Tr (hereinafter this state is referred to as a substantially-mated state).

Therefore, as shown in the example of FIG. 2B, even when the absorbent main body 10 (10a) is continuously supplied from the cutter roll device with no or a narrow space between the absorbent main bodies 10 and 10*a* adjacent in the revolving direction, the holding pads 35 can immediately receive the absorbent main body 10 while maintaining the space between the absorbent main bodies 10 and 10*a*.

Note that, concerning setting of the configuration so that in the substantially-mated state the downstream end 35*e*1 of the holding pad 35 passes the receiving position Qin, the setting can be made by setting the annular shape (e.g., elliptical shape) of the first rail 50 and the second rail 62, and the planar positions of the rails 50 and 62 or the like. The planar positional relationship will be described later.

On the other hand, as shown in FIGS. 2A and 2C, at the discharge position Qout, a pressing roll device 120 is arranged. The pressing roll device 120 has one pressing roll 120 which is arranged above the holding pad 35 in the straight-line path TrL of the orbit Tr; the pressing roll 120 is supported so as to be driven and rotate about an axis C120 along the CD direction. Also, the pressing roll 120 has a perfect circular cross section and is a flat roll whose outer circumferential surface is flat throughout the CD direction. Further, the pressing roll 120 is urged downward by a pressure appropriate for the outer circumferential surface of the roll 120 to be brought lightly against the holding surface 35*a* of the holding pad 35 when the holding surface 35*a* passes the discharge position Qout. Around the pressing roll 120, the pair of band members 20 and 24 lined up in the CD direction are wrapped in a form of the continuous bodies 20*a* and 24*a*. The pair of band members 20 and 24 are running at a certain running speed.

Further, onto either of both end sections 10*e* and 10*e* of the absorbent main body 10 in the CD direction or continuous bodies 20*a* and 24*a* of the band members with which the end sections 10*e* and 10*e* are to be in contact, hot-melt adhesive is applied in advance. As shown in FIGS. 2A and 2C, when the holding pad 35 passes the discharge position Qout backward in the MD2 direction (corresponding to the running direction) while the longitudinal direction of the pad 35 is pointing in the CD direction due to the spin motion and the like, the end sections 10*e* and 10*e* of the absorbent main body 10 in the CD direction adhere to the corresponding continuous bodies 20*a* and 24*a* of the band members. Therefore, the absorbent main body 10 is discharged to the continuous bodies 20*a* and 24*a* of the band members from the holding surface 35*a*.

As mentioned above, the holding surface 35*a* of the holding pad 35 is a horizontal plane in a substantially entire area thereof, the holding surface 35*a* is moving in the same horizontal plane as mentioned above based on the orbit Tr, and the spin motion of the holding pad 35 is performed in the same horizontal plane. Therefore, a clearance between the holding surface 35*a* and the outer circumferential surface of the pressing roll 120 is equally spaced through the entire length thereof in the CD direction (a direction perpendicular to the paper surface in FIG. 2C). In addition, when the portions of the holding surface 35*a* passes the discharge position Qout along the MD2 direction which is the passing direction, the abovementioned clearance is maintained to be equally spaced through the entire length thereof in the MD2 direction of the holding surface 35*a*. This can effectively prevent the absorbent main body 10 from creasing when the body 10 is discharged.

However, as mentioned above, in some cases, the holding pad 35 may have a horizontal plane section only on a part of the holding surface 35*a* not on the entire surface thereof; in other words, the holding surface 35*a* may have some irregularities and slopes partially on other area than the horizontal plane section. In this case, in the same way as mentioned above, it is desirable that the peripheral area of the holding surface 35*a* is a horizontal plane section in a flame-like shape. With this configuration, based on at least both end sections in the CD direction within the peripheral area, both end sections 10*e* and 10*e* of the absorbent main body 10 in the longitudinal direction are pressed onto and brought against the pressing roll 120 with the abovementioned clearance being equally spaced, the end sections 10*e* and 10*e* being sections which adhere to the continuous bodies 20*a* and 24*a* of the band member. This effectively prevents the end sections 10*e* and 10*e* from creasing.

Incidentally, the speed at which the holding pad 35 is passing forward in the MD2 direction at the receiving position Qin is maintained within a range from the speed at which the absorbent main body 10 (10*a*) is transported from the cutter roll device 100 to a slightly faster speed (inclusive). Thus, when the holding pad 35 receives the absorbent main body 10 from the anvil roll 102 of the cutter roll device 100, the holding pad 35 receives the absorbent main body 10 (10*a*) while extending the body 10 (10*a*) slightly. This makes it possible to suppress further the creasing of the absorbent main body 10 (10*a*) when being received.

The speed at which the holding pad 35 is passing backward in the MD2 direction at the discharge position Qout is maintained within a range from a speed at which the continuous bodies 20*a* and 24*a* of the band members are running and a slightly slower speed (inclusive). Thus, when the holding pad 35 discharges the absorbent main body 10 to the continuous bodies 20*a* and 24*a* of the band members, the absorbent main body 10 is discharged while being slightly extended by the continuous bodies 20*a* and 24*a* of the band members. This makes it possible to suppress further the creasing of the absorbent main body 10 when being discharged.

The abovementioned setting of the passing speed of the holding pad 35 within the speed range can be made by setting the angular speed of the rotation of the turning table 45, the path of the orbit Tr or the like.

Figure 9:
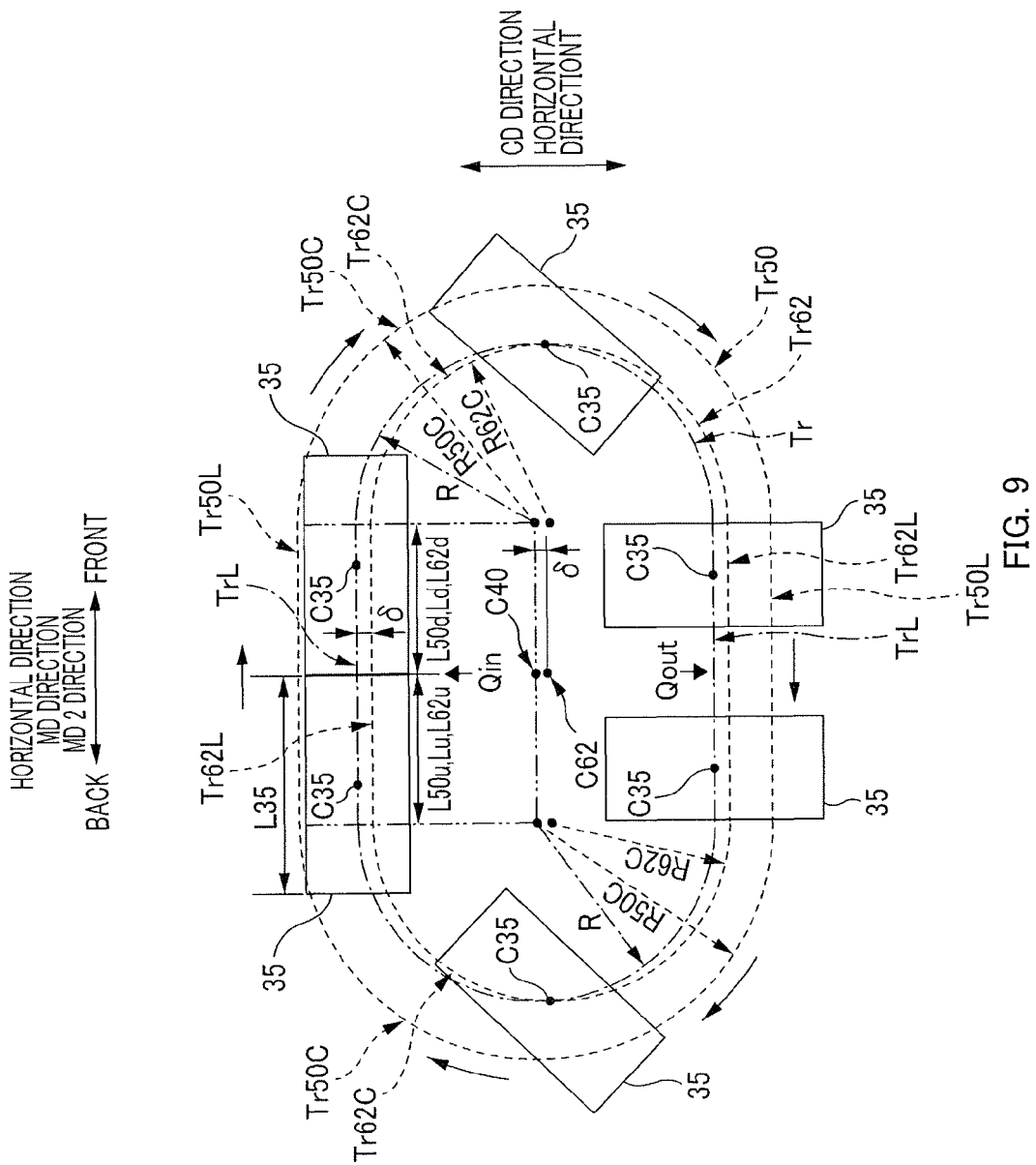
FIG. 9 is an explanatory diagram showing the planar positional relationship of the orbit Tr of the holding pad 35, a first rail 50, and a second rail 62.
Figure 10A:
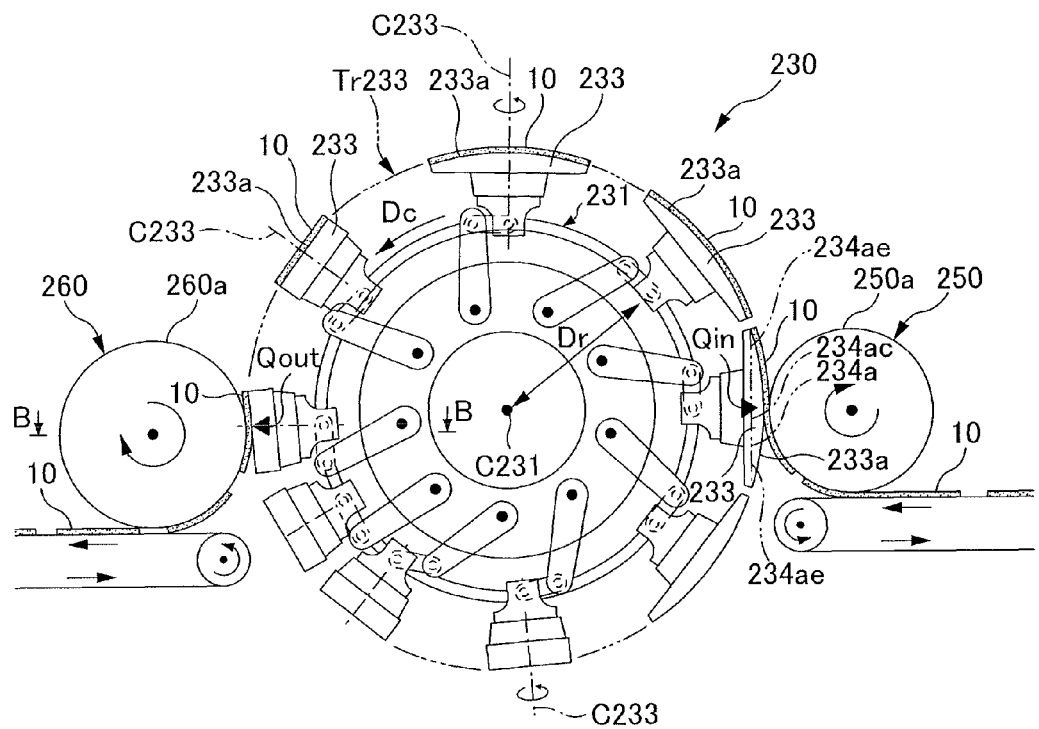
FIG. 10A is a side view of the conventional 90-degree turning drum apparatus 230.
Figure 10B:
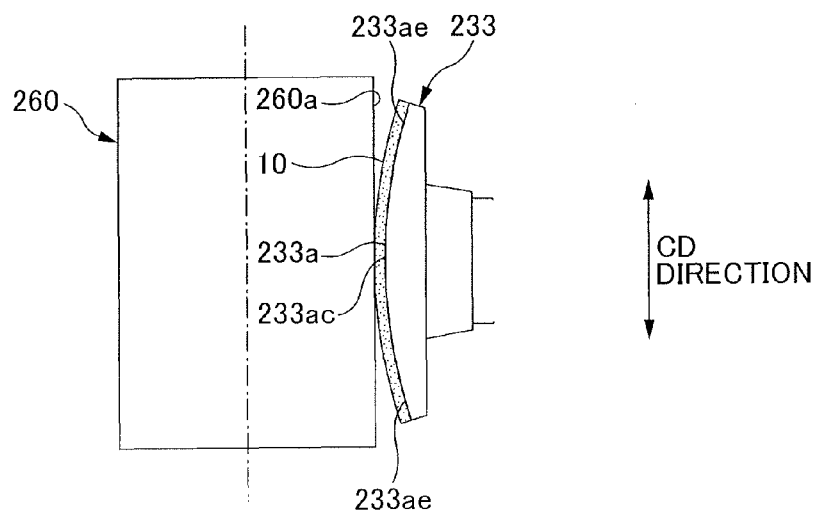
FIG. 10B is a view along arrows B-B in FIG. 10A.

FIG. 9 is an explanatory diagram showing the planar positional relationship of the orbit Tr of the holding pad 35, the first rail 50, and the second rail 62. In the figure, concerning the first rail 50 and the second rail 62, only the center lines thereof are indicated.

Both the first rail 50 and the second rail 62 have a orbit whose shape is elliptical similar to the orbit Tr of the holding pad 35 mentioned above. That is, the first rail 50 includes: a pair of semicircular paths Tr50C and Tr50C of a radius R50C on both end sections in the front-and-back direction (MD2 direction); two parallel straight-line paths Tr50L and Te50L connecting the foregoing semicircular paths Tr50C and Tr50C along the front-and-back direction. Also, the second rail 62 includes: a pair of semicircular paths Tr62C and Tr62C of a radius R62C on both end sections in the front-and-back direction (MD2 direction); two parallel straight-line paths Tr62L and Tr62L connecting the foregoing semicircular paths Tr62C and Tr62C along the front-and-back direction.

The first rail 50 is set to be coaxial with the revolution axis C40, which is the planar center of the orbit Tr. The first rail 50 is larger than the orbit Tr and is arranged surrounding the orbit Tr from the outside thereof. Therefore, the first arm member 55 orbits in an outer path than the orbit Tr. On the other hand, though the second rail 62 has the same shape as the orbit Tr, the second rail 62 is positioned differently from the orbit Tr by a predetermined offset value 6 in the CD direction. In other words, though the planar center C62 of the second rail 62 is at the same position as the revolution axis C40 with respect to the MD2 direction, it is positioned differently from the revolution axis C40 by the foregoing offset value 6 with respect to the CD direction. Combination of the first rail 50 and the second rail 62 mentioned above enables the holding pad 35 to revolve along the orbit Tr and to spin according to its position in the orbit Tr, as mentioned above.

The foregoing sections describes that while passing the receiving position Qin, the longitudinal direction of the holding pad 35 and the passing direction are fixed and maintained in the front-and-back direction (MD2 direction) in which the absorbent main body 10 is transported at the receiving position. This is realized based on the following setting of the first and second rails 50 and 62.

One of straight-line paths Tr50L in the first rail 50 is arranged extending across the receiving position Qin in the MD2 direction. At the receiving position Qin, the upstream-side length L50u and the downstream-side length L50d of that straight-line path Tr50L are set to equal to or more than half of the longitudinal length L35 of the holding pad 35 (=L35/2).

Thus, the straight-line path TrL of the orbit Tr also extends across the receiving position Qin in the MD2 direction. In addition, at the receiving position Qin, the upstream-side length Lu and the downstream-side length Ld of this straight-line path TrL are also set to equal to or more than half of the length L35 (=L35/2). Therefore, when passing the receiving position Qin, the holding pad 35 moves straight in the front-and-back direction (MD2 direction) through the entire longitudinal length L35 in the passing direction of the holding pad 35; thereby, the holding pad 35 moves quickly in the transporting direction of the absorbent main body 10.

On the other hand, One of straight-line path Tr62L in the second rail 62 is arranged extending across the receiving position Qin in the MD2 direction. At the receiving position Qin, the upstream-side length L62u and the downstream-side length L62d of that straight-line path Tr62L are set to equal to or more than half of the longitudinal length L35 of the holding pad 35 (=L35/2). This allows the holding pad 35 to pass the receiving position Qin in the MD2 direction while the longitudinal direction of the holding pad 35 is maintained in the MD2 direction. Therefore, the passing motion at the receiving position Qin mentioned above can be achieved.

Note that, at the discharge position Qout, the other straight-line path Tr50L in the first rail 50 extends across the discharge position Qout in the MD2 direction. Therefore, the holding pad 35 can move at the discharge position Qout along the MD2 direction, which is the transporting direction of the absorbent main body 10. Further, the other straight-line path Tr62L in the second rail 62 extends across the discharge position Qout in the MD2 direction. This allows the holding pad 35 to pass the discharge position Qout while the longitudinal direction of the holding pad 35 is maintained in the CD direction. Therefore, the smooth discharge operation of the absorbent main body 10 mentioned above can be achieved.

Other Embodiments

While the embodiments according to the invention are described above, the invention is not limited to the embodiments and can be altered as described below.

In the foregoing embodiment, using means such as the second rail 62 and the second arm member 64, the spin motion of each holding pad 35 is produced based on the rotating motion of the turning table 45. However, the invention is not limited thereto. For example, the holding pad 35 may be caused to spin as follows: a power source such as a servo motor is disposed for each holding pad 35 and the servo motor is driven and rotates under control. However, in this configuration, the same number of servo motors as the holding pads 35 are needed, and also a controller which controls the spin motion in synchronization with the rotation angle of the turning table 45 is needed. Therefore, in order to simplify the configuration of the apparatus or to reduce costs, the foregoing embodiment is more desirable.

In the foregoing embodiment, rail members such as the first rail 50 and the second rail 62 are used for the revolution mechanism 40 and the spin mechanism 60. However, the invention is not limited thereto. These mechanism may be composed of a cam mechanism, etc. For example, the following configuration may be employed: on the upper surface of the turning table 45, two elliptical grooved cams are disposed; the cam follower 57 of the first arm member 55 associated with the pad supporting section 52 is inserted into one of the grooved cams and rolls; and the cam follower 67 of the second arm member 64 associated with the holding pad 35 is inserted into the other grooved cam and rolls.

In the foregoing embodiment, though the plane section which is the holding surface 35a of the holding pad 35 is a horizontal plane, the invention is not limited thereto. The plane section may slightly be tilted from the horizontal plane. However, as a matter of course, even in this case, the spin axis C35 and the revolution axis C40 are set so as to satisfy the relationship that the spin axis C35 and the revolution axis C40 are parallel to the normal direction of the plane section.

In the foregoing embodiment, elliptical rail members are provided as an example of the first rail 50 and the second rail 62. However, the invention is not limited thereto. Depending on the arrangement of the receiving position Qin and the discharge position Qout, the receiving and discharge operations and the like, the rail member having any appropriate shape other than the abovementioned elliptical shape may be employed.

In the foregoing embodiment, at the discharge position Qout, the passing apparatus 30 discharge the absorbent main body 10 (the first sheet-like workpiece) directly to the continuous bodies 20a and 24a of the band member (the second sheet-like workpiece) However, the invention is not limited thereto. For example, the holding pad 35 may discharge the first sheet-like workpiece to other means, such as a suction roll, arranged at the discharge position Qout. Note that, the suction roll in the above example is a flat roll which is driven and rotates about an axis along the CD direction; and also the suction roll has a plurality of suction holes formed on its outer circumferential surface and can hold the first sheet-like workpiece by suction from the suction holes in surface-to-surface contact with the foregoing outer circumferential surface.

In the foregoing embodiment, as an example of an absorbent article, the disposable diaper 1 is provided. However, the invention is not limited thereto as long as an article absorbs a excreted fluid or a bodily fluid. For example, the passing apparatus 30 of the present embodiment may be applied to a manufacturing line of sanitary napkins.

Though no description is given in the foregoing embodiment, in some cases, a support member 90 which supports at the peripheral area 45e of the turning table 45 the weight of the peripheral area 45e may be arranged at a plurality of appropriate positions in the rotating direction Dc of the turning table 45, as shown in FIG. 6A. As an example of the configuration of the support member 90, there is one which includes a stay member 91 and a roller member 93, the stay member 91 standing on the upper surface of the fixed table 41, the roller member 93 being arranged on the upper end of the stay member 91 rotatable about the horizontal axis. The support member 90 supports the peripheral area 45e of the turning table 45 by abutting the peripheral area 45e from below with the roller member 93 of the support member 90. This can prevent the peripheral area 45e of the turning table 45 from hanging due to its own weight.

In the foregoing embodiment, the spin motion is not described in detail. As shown in FIGS. 3A to 3F, during one revolution in the orbit Tr, each holding pad 35 is configured to spin about the spin axis C35 only once (only 360°). Therefore, of both ends of the holding pad 35 in the longitudinal direction, one end is defined as a first end 35e1 and the other end is defined as a second end 35e2, when the holding pad 35 passes the receiving position Qin, the first end 35e1 is always positioned downstream of the second end 35e2 in the revolving direction. Therefore, as shown in FIG. 2A, at the receiving position Qin, always the first end 35e1 receives the front end section 10e1 of the absorbent main body 10 and the second end 35e2 receives the back end section 10e2. Thus, conditions such as the surface of the first end 35e1 can be set to conditions optimal to receive the front end section 10e1 of the absorbent main body 10, and conditions such as the surface of the second end 35e2 can be set to conditions optimal to receive the back end section 10e2. This can prevent more effectively the absorbent main body 10 from creasing when the holding pad 35 receives the absorbent main body 10.

Figure 3A:
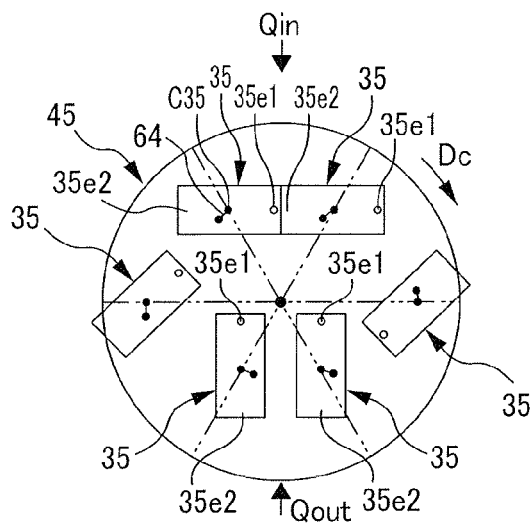
FIGS. 3A to 3F are top views showing revolving and spinning unit motions of the holding pads 35.
Figure 3D:
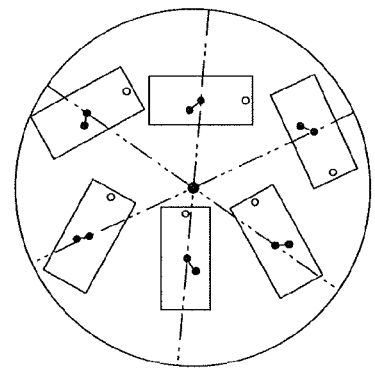
Figure 3B:
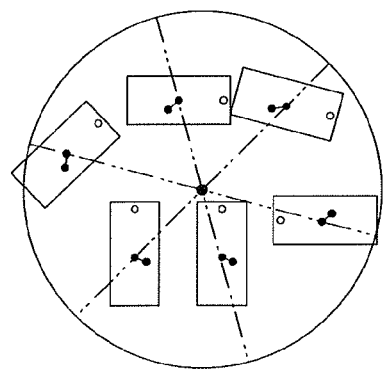
Figure 3E:
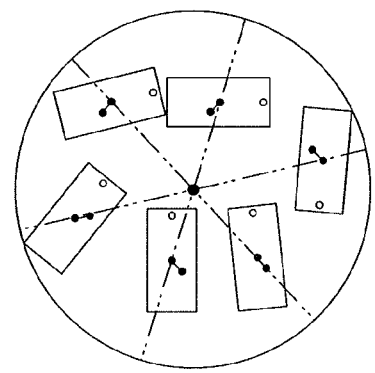
Figure 3C:
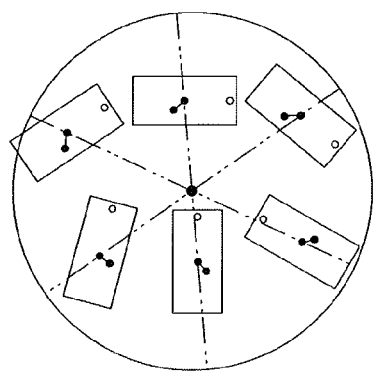
Figure 3F:
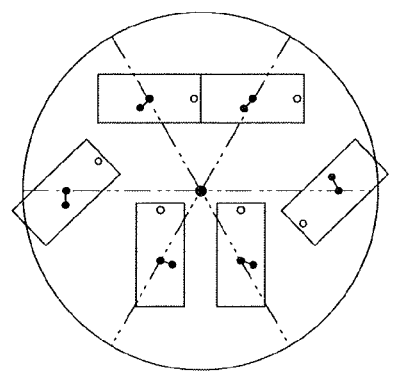

Note that, in the same manner as mentioned above, the correspondence between both ends of the holding pad 35 and the workpiece is fixed at the discharge position Qout. In other words, as shown in FIG. 3A, of both ends of the holding pad 35 in the longitudinal direction, one end is defined as a third end 35e1 and the other end is defined as a fourth end 35e2, when the holding pad 35 passes the discharge position Qout, the third end 35e1 is always positioned inward from the fourth end 35e2 with respect to the orbit Tr. Therefore, concerning the pressing roll 120 (FIG. 2A) arranged at the discharge position Qout, the inside portion and the outside portion with respect to the orbit Tr respectively correspond to the third end 35e1 and the fourth end 35e2 of the holding pad 35. That is, as shown in FIG. 2A, the correspondence is as follows: the third end 35e1 discharges the front end section 10e1 of the absorbent main body 10 to the continuous body 24a of the back-side band member 24, and the fourth end 35e2 discharges the back end section 10e2 of the absorbent main body 10 to the continuous body 20a of the stomach-side band member. Thus, conditions such as the surface of the third end 35e1 can be set to conditions optimal to discharge the body 10 to the continuous body 24a of the back-side band member 24, and conditions such as the surface of the fourth end 35e2 can be set to conditions optimal to discharge to the continuous body 20a of the stomach-side band member. This can prevent more effectively the absorbent main body 10 from creasing when the holding pad 35 discharges the absorbent main body 10 to the continuous bodies 20a and 24a of the band members.

As mentioned above, the spin motion of the holding pad 35 is achieved by means such as setting the planar shape of the second rail 62 serving as the main part of the spin mechanism 60 to appropriate proportion to the first rail 50 serving as the main part of the revolution mechanism 40.

REFERENCE SIGNS LIST 1 disposable diaper (absorbent article),
1a semifinished product,
3 torso opening,
5 leg opening,
10 absorbent main body (first sheet-like workpiece),
10a continuous body of absorbent main body (first sheet-like workpiece),
10e end section,
10e1 front end section,
10e2 back end section,
11 absorbent body,
12 surface sheet member,
13 back face sheet member,
14 leakage-proof sheet,
15 exterior sheet,
17 elastic member,
20 stomach-side band member,
20a continuous body of stomach-side band member (second sheet-like workpiece),
21 nonwoven fabric,
24 back-side band member,
24a continuous body of back-side band member (second sheet-like workpiece),
30 passing apparatus,
35 holding pad,
35a holding surface,
35e1 downstream end (first end, third end),
35e2 upstream end (second end, fourth end),
35h suction hole,
35k opening sections,
36 shaft,
40 revolution mechanism,
41 fixed table (fixed bed),
42 bearing,
45 turning table,
45a shaft,
45h opening,
45p pulley,
45e peripheral area,
48 power source,
48a drive shaft,
48b timing belt,
48p pulley,
48m servo motor,
50 first rail,
52 pad supporting section,
52a cylindrical member,
52b no-top-bottom-closed cylinder,
53 bearing,
55 first arm member,
56 bearing,
57 cam follower,
59 guide member,
59a linear guide rail,
59b guide block,
60 spin mechanism,
62 second rail,
64 second arm member,
64a linking member,
64b engaging member,
64c bearing member,
67 cam follower,
80 suction mechanism,
82 negative-pressure chamber drum,
82a cylindrical member,
82b cover plate,
82c cover plate,
82h through hole,
83 suction duct,
84 suction hose,
84a hose opening on one end,
84b hose opening on the other end,
90 support member,
91 stay member,
93 roller member,
100 cutter roll device, 101 cutter roll,
101k cutter blade,
102 anvil roll,
120 pressing roll (pressing roll device),
C10 center,
C35 spin axis,
C40 revolution axis,
C45 rotation center (first axis),
C62 planar center,
C100 axis,
C120 axis,
Qin receiving position, Qout discharge position,
S35 space,
S52b inner space,
S82 substantially-closed space,
Tr orbit,
Tr50C semicircular path,
Tr50L straight-line path,
Tr62C semicircular path,
Tr62L straight-line path,
Dc rotating direction,
Dr rotation-radius direction,
R radius,
R500 radius,
R62C radius

The invention claimed is:

1. A passing apparatus of a workpiece associated with an absorbent article that
receives at a receiving position a first sheet-like workpiece being transported in a transporting direction,
changes a longitudinal direction of the first sheet-like workpiece to a direction that intersects the longitudinal direction of the timing when the first sheet-like workpiece is received at the receiving position, and
discharges at a discharge position the first sheet-like workpiece whose longitudinal direction is changed,
comprising:
a plurality of holding pads having a plane section that is in contact with a surface of the first sheet-like workpiece and holds the first sheet-like workpiece;
a revolution mechanism that causes the holding pad to revolve about a revolution axis parallel to a normal direction of the plane section; and
a spin mechanism that causes the holding pad to spin about a spin axis parallel to the normal direction of the plane section, wherein
on an orbit of the holding pad determined by the revolution mechanism, the receiving position and the discharge position are set,
at the receiving position, the longitudinal direction of the first sheet-like workpiece points in the transporting direction,
the holding pad includes a holding surface in which the plane section is included,
the holding surface is formed so that a longitudinal direction and a width direction thereof are respectively aligned with a longitudinal direction and a width direction of the holding pad,
the holding pad passes the receiving position on the orbit by a movement of the holding pad along the transporting direction in a state where the spin mechanism causes the longitudinal direction of the holding pad to point in a direction parallel to the transporting direction of the first sheet-like workpiece,
the holding pad passes the discharge position on the orbit by a movement of the holding pad in the direction parallel to the transporting direction in a state where the spin mechanism causes the longitudinal direction of the holding pad to point in a direction perpendicular to the longitudinal direction of the holding pad at the receiving position,
when a downstream end of the holding pad in a revolving direction passes the receiving position, the holding pad associated with the downstream end is in a straight line with an adjacent holding pad positioned on a downstream side of the holding pad in the revolving direction and a space between the downstream end and an upstream end of the adjacent holding pad becomes smallest within an entire edge of the orbit, and
after the downstream end passes the receiving position, the space is enlarged.

2. A passing apparatus of a workpiece associated with an absorbent article according to claim 1, wherein
the revolution mechanism includes
a rotating member that is driven and rotates about a first axis parallel to the revolution axis, and
a drive mechanism that changes a rotation radius of the holding pad from the first axis based on a rotating motion of the rotating member, the holding pad rotating about the first axis together with the rotating member.

3. A passing apparatus of a workpiece associated with an absorbent article according to claim 1, wherein
the orbit has a straight-line path along the transporting direction,
the receiving position is set in the straight-line path, and
an upstream section and a downstream section of the straight-line path at the receiving position each have a length equal to or more than half of a longitudinal length of the holding pad.

4. A passing apparatus of a workpiece associated with an absorbent article according to claim 1, wherein
at the receiving position, the transporting direction of the first sheet-like workpiece is parallel to a moving direction of the holding pad,
at the discharge position, the holding pad discharges the first sheet-like workpiece to a second sheet-like workpiece running at the discharge position, and
at the discharge position, a running direction of the second sheet-like workpiece is parallel to the moving direction of the holding pad.

5. A passing apparatus of a workpiece associated with an absorbent article according to claim 4, wherein
the absorbent article is a diaper,
the first sheet-like workpiece is an absorbent main body that is brought into contact with a crotch of a wearer and absorbs a bodily fluid when the diaper is worn,
the second sheet-like workpiece is a member that covers a waist of the wearer and fixes the absorbent main body to the wearer when the diaper is worn, and
the transporting direction of the first sheet-like workpiece at the receiving position is parallel to the running direction of the second sheet-like workpiece at the discharge position.

6. A passing apparatus of a workpiece associated with an absorbent article according to claim 1, wherein
the orbit has a straight-line path along the transporting direction,
the receiving position is set in the straight-line path.

7. A passing apparatus of a workpiece associated with an absorbent article according to claim 1, wherein
of both ends of the holding pad in the longitudinal direction, one end is defined as a first end and another end is a second end, and when the holding pad passes the receiving position, the spin mechanism adjusts an orientation of the holding pad so that the first end is always positioned downstream of the second end in the revolving direction.

8. A passing apparatus of a workpiece associated with an absorbent article according to claim 1, wherein
of both ends of the holding pad in the longitudinal direction, one end is defined as a third end and another end is a fourth end, and
when the holding pad passes the discharge position, the spin mechanism adjusts an orientation of the holding pad so that the third end is always positioned inward from the fourth end with respect to the orbit.

* * * * *